(12) United States Patent
Yoneda et al.

(10) Patent No.: US 8,436,878 B2
(45) Date of Patent: May 7, 2013

(54) IMAGE FORMING APPARATUS

(75) Inventors: Kazuhisa Yoneda, Osaka (JP); Hiroyuki Nagao, Osaka (JP); Hidenobu Mandai, Osaka (JP); Kazuhiro Matsuyama, Osaka (JP); Yasushi Nakamura, Osaka (JP); Yoshiya Kinoshita, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 481 days.

(21) Appl. No.: 12/702,488

(22) Filed: Feb. 9, 2010

(65) Prior Publication Data

US 2010/0201775 A1    Aug. 12, 2010

(30) Foreign Application Priority Data

Feb. 9, 2009   (JP) .................................. 2009-027352

(51) Int. Cl.
*B41J 2/415* (2006.01)
*A62B 7/08* (2006.01)

(52) U.S. Cl.
USPC .......................................... 347/123; 422/121

(58) Field of Classification Search .................. 347/123; 422/121
See application file for complete search history.

(56) References Cited

U.S. PATENT DOCUMENTS

| 6,447,731 | B1 * | 9/2002 | Sun et al. ...................... 422/121 |
| 7,672,012 | B2 * | 3/2010 | Silverbrook ................... 358/1.8 |
| 7,854,900 | B2 * | 12/2010 | Takeda et al. ................. 422/120 |
| 8,033,515 | B2 * | 10/2011 | Martin et al. ............ 248/224.61 |
| 2003/0072675 | A1 | 4/2003 | Takeda et al. |

FOREIGN PATENT DOCUMENTS

| JP | 2002-19223 A | 1/2002 |
| JP | 2002-226070 A | 8/2002 |
| JP | 2004-169964 A | 6/2004 |
| JP | 2004-233618 A | 8/2004 |
| JP | 2005-4144 A | 1/2005 |
| JP | 2006-126250 A | 5/2006 |
| JP | 2006-343491 A | 12/2006 |

* cited by examiner

*Primary Examiner* — Omar Rojas
(74) *Attorney, Agent, or Firm* — Birch, Stewart, Kolasch & Birch, LLP

(57) ABSTRACT

An image forming apparatus in one embodiment of the present invention is an image forming apparatus that includes a main body that performs processing to form an image on a recording paper, the image forming apparatus including, an ion generating section that is external to the main body, generates ions and emits those ions to the outside.

5 Claims, 15 Drawing Sheets

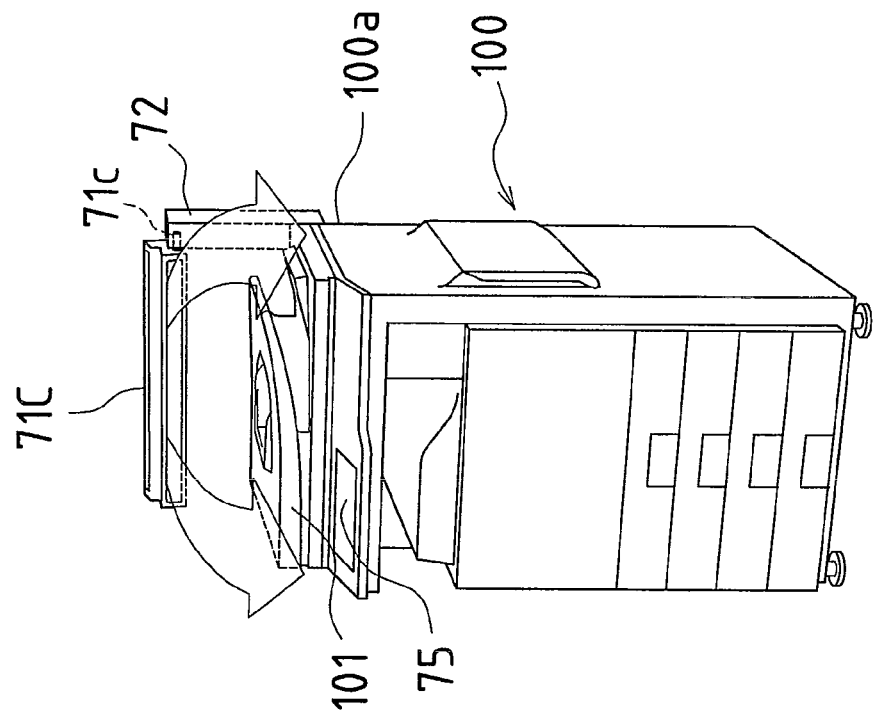
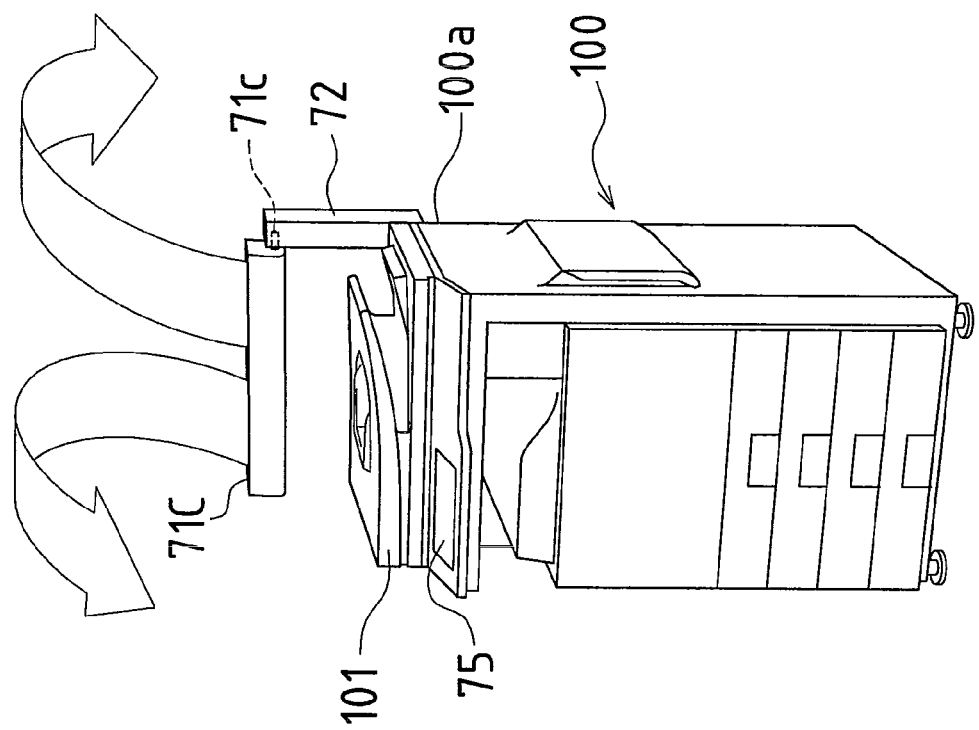
FIG.7,8

IMAGE FORMING APPARATUS

BACKGROUND OF THE INVENTION

1. Field of the Invention

This application claims priority under 35 U.S.C. §119(a) on Patent Application No. 2009-027352 filed in Japan on Feb. 9, 2009, the entire contents of which are herein incorporated by reference.

2. Description of the Related Art

The present invention relates to an image forming apparatus that includes an ion generating function in an apparatus that performs processing to form an image, such as a copy machine, printer, or facsimile apparatus.

Recently, electrophotographic image forming apparatuses capable of image forming, such as copy machines, printers, and facsimile apparatuses, have been developed. These image forming apparatuses perform processing to form an image on a recording paper. That is, in such an image forming apparatus, for example, an electrostatic latent image is formed on the surface of a photosensitive drum, this electrostatic latent image is developed using toner to form a toner image on the surface of the photosensitive drum, the toner image is transferred from the photosensitive drum to a recording paper, and heat and pressure are applied to the recording paper to fix the toner image on the recording paper.

In such an image forming apparatus, a harmful exhaust gas may sometimes be produced during the processing to form an image on the recording paper. A main component of this exhaust gas is known to be longifolene or the like generated from the recording paper.

However, image forming apparatuses are indispensible office automation devices in offices and the like, and therefore are installed in nearly all offices, and are furthermore spreading to homes and hospitals. Therefore, harmful exhaust gas discharged from an image forming apparatus causes discomfort to many users.

Consequently, there have been various proposals for achieving purification of such harmful exhaust gas in an image forming apparatus (for example, see JP 2005-4144A, referred to below as Patent Document 1). Patent Document 1 discloses an image forming apparatus in which an air-blowing fan, a minus-ion generating unit, a positively charged filter, and so forth are provided within the image forming apparatus. In this image forming apparatus, toner particles and dust generated within the apparatus are negatively charged, and the negatively charged toner particles and dust are attracted to the positively charged filter, thus reducing the amount of harmful substances emitted outside of the apparatus.

On the other hand, air cleaning devices that purify air within a room have become widespread in offices, homes, hospitals, and the like, and there are various such air cleaning devices (for example, see JP 2002-58731A, referred to below as Patent Document 2). The air cleaning device disclosed in Patent Document 2 simultaneously generates positive and negative ions, and airborne bacteria in the air is effectively removed by the positive and negative ions.

However, with the image forming apparatus disclosed in Patent Document 1, it is necessary to provide the minus-ion generating unit and the positively charged filter, which are not directly necessary for the image forming function of this image forming apparatus, within the image forming apparatus, causing increased size and cost of the image forming apparatus.

Also, with the air cleaning device disclosed in Patent Document 2, even if the air within a room can be purified, the main focus of this air cleaning device is not purification of harmful exhaust gas discharged from the image forming apparatus.

Moreover, it is expensive to provide both a costly image forming apparatus as disclosed in Patent Document 1 and an air cleaning device as disclosed in Patent Document 2.

Therefore, there have been demands for an image forming apparatus whereby it possible to suppress the discharge of harmful exhaust gas as described above by purifying the exhaust gas in the image forming apparatus, and also possible to purify the air of the room in which the image forming apparatus is installed, so that it is not necessary to install an air cleaning device in the room in which the image forming apparatus is installed.

SUMMARY OF THE INVENTION

The present invention was made in order to respond to such demands, and aims to provide an image forming apparatus whereby while suppressing an increase in cost and size of the image forming apparatus, it is possible to purify harmful exhaust gas discharged from the image forming apparatus, and also possible to purify the air of the room in which the image forming apparatus is installed.

The inventors of the present invention, with respect to purification of harmful exhaust gas discharged from an image forming apparatus, found that it is possible to purify harmful exhaust gas discharged from an image forming apparatus, depending on the ion emission method, even by generating and emitting ions outside of the image forming apparatus, rather than providing a minus-ion generating unit, a filter, and so forth within the image forming apparatus, as in the case of the image forming apparatus disclosed in Patent Document 1. The present invention was made based on this original idea.

The image forming apparatus of the present invention originated in this way is provided with features as follows. That is, the image forming apparatus of the present invention is an image forming apparatus that includes a main body that performs processing to form an image on a recording paper, the image forming apparatus including, an ion generating section that is external to the main body of the image forming apparatus, generates ions and emits those ions to the outside.

In the above image forming apparatus, the main body of the image forming apparatus is a portion that performs image forming processing in the image forming apparatus, and an ion generating section is not included in the main body of the image forming apparatus. Ordinarily, the main body of the image forming apparatus is provided with an independent case.

According to the above image forming apparatus, by providing an ion generating section external to the main body of the image forming apparatus, it is not necessary to provide an ion generating section inside of the image forming apparatus, so it is possible to suppress an increase in the size of the image forming apparatus.

Therefore, while suppressing an increase in cost and size of the image forming apparatus, as described below, it is possible to purify harmful exhaust gas discharged from the image forming apparatus, and also possible to purify the air of the room in which the image forming apparatus is installed. That is, a single device can serve both the role of purifying exhaust gas from the image forming apparatus and purifying air within the room. Accordingly, it is possible to eliminate the need to separately provide an air cleaning device in the room in which the image forming apparatus has been installed.

In the above image forming apparatus, the ion generating section may by attached while spaced-apart from the main body of the image forming apparatus.

In this case, the ion generating section may be supported by a support member provided protruding upward from the main body of the image forming apparatus.

Furthermore, the support member may be provided protruding upward from a corner portion on an upper side of a rear face of the main body of the image forming apparatus, and support a base end of the ion generating section disposed perpendicular to the support member at a tip end of the support member.

Alternatively, the support member may be provided protruding upward from a center portion on an upper side of a rear face of the main body of the image forming apparatus, and support a center portion of the ion generating section disposed perpendicular to the support member at a tip end of the support member.

In the above image forming apparatus, the side of the main body of the image forming apparatus on the side where an operator who operates the image forming apparatus performs operation is referred to as the front face of the main body of the image forming apparatus, and the face on the opposite side opposing the front face is referred to as the rear face of the main body of the image forming apparatus. Ordinarily, an operating panel used to perform operation of the image forming apparatus is provided on the front face side of the main body of the image forming apparatus. The longitudinal direction of the ion generating section is the same as the direction that vertically intersects the front-rear direction of the main body of the image forming apparatus in the horizontal plane.

As described above, by attaching the ion generating section, it is possible to easily provide the ion generating section external to the main body of the image forming apparatus. Also, the space necessary for operating the image forming apparatus can be adequately secured, so that a configuration can be adopted whereby operability of the image forming apparatus is not impaired.

In the above image forming apparatus, it is preferable that the ion generating section can vary the amount of ions generated and emitted by the ion generating section according to whether the image forming apparatus is operating or in standby. The operating state of the image forming apparatus refers to a time when the main body of the image forming apparatus is performing processing to form an image on a recording paper, and the standby state refers to any other time.

By adopting the above sort of configuration, as described below, it is possible to efficiently perform purification of harmful exhaust gas discharged from the image forming apparatus, and purification of air in the room where the image forming apparatus has been installed.

In order to enable varying of the amount of ions generated and emitted by the above ion generating section, specifically, for example, the ion generating section can include a fan, and the amount of ions emitted can be varied by changing the air volume from this fan.

Alternatively, the ion generating section may include a plurality of ion generators, and vary the amount of ions emitted by increasing or decreasing the number of ion generators caused to operate.

By adopting such a configuration, it is possible to easily and reliably vary the amount of ions generated and emitted by the ion generating section.

In the above image forming apparatus, the amount of ions generated and emitted by the ion generating section may be less when the image forming apparatus is in standby than when the image forming apparatus is operating. The reason for adopting such a configuration is as follows.

That is, during operation of the image forming apparatus, because the image forming apparatus is operating, it is necessary not only to purify air within the room where the image forming apparatus is installed, but also to purify harmful exhaust gas discharged from the image forming apparatus.

Therefore, by adopting the above sort of configuration, it is possible for the ion generating section to emit more ions to the outside when the image forming apparatus is operating than when the image forming apparatus is in standby, and so it is possible to both purify harmful exhaust gas discharged from the image forming apparatus and also purify air in the room where the image forming apparatus has been installed.

On the other hand, during standby of the image forming apparatus, it is sufficient to only purify air in the room where the image forming apparatus has been installed; it is not necessary to purify harmful exhaust gas discharged from the image forming apparatus. Consequently, it is possible for the ion generating section to emit fewer ions when the image forming apparatus is in standby than when the image forming apparatus is operating. Therefore, it is possible to efficiently emit ions in the image forming apparatus.

In the above image forming apparatus, opposite to the above scheme, the following sort of configuration may also be adopted. That is, the amount of ions generated and emitted by the ion generating section may be less when the image forming apparatus is operating than when the image forming apparatus is in standby.

In this sort of scheme, it is possible to adopt a method in which, for example, by the air volume from a fan being less when during operation of the image forming apparatus than during standby of the image forming apparatus, it is possible to allow ions to be dispersed around the image forming apparatus.

That is, a configuration is adopted in which the surroundings of the image forming apparatus are covered with air including ions, in the manner of an air curtain. By adopting such a configuration, it is possible to reliably purify harmful exhaust gas discharged from the image forming apparatus.

The above scheme is based on usage when the following sort of states are assumed. That is, during operation of the image forming apparatus, the apparatus is mainly dedicated to purification of harmful exhaust gas discharged from the image forming apparatus, and during standby of the image forming apparatus, the apparatus purifies air in the room where the image forming apparatus has been installed.

Ordinarily, the volume of the image forming apparatus is small relative to the volume of the room where the image forming apparatus has been installed, so it is considered acceptable for the amount of ions necessary for purification of harmful exhaust gas discharged from the image forming apparatus to be less than the amount of ions necessary for purifying air within the room where the image forming apparatus has been installed. Consequently, a configuration is adopted in which the amount of ions generated and emitted by the ion generating section is less during operation of the image forming apparatus than during standby of the image forming apparatus.

Ordinarily, a tendency is seen for the time during which the ion generating section is operating to be much less than the time during which the image forming apparatus is in standby. Consequently, even if a configuration is adopted in which during operation of the image forming apparatus, the apparatus is mainly dedicated to purification of harmful exhaust gas discharged from the image forming apparatus, and during standby of the image forming apparatus, the apparatus is mainly dedicated to purification of air in the room where the image forming apparatus has been installed, it is conceivable that there will be substantially no adverse effects due to not effectively purifying air in the room where the image forming apparatus has been installed during operation of the image forming apparatus. The above scheme was conceived from this sort of perspective.

By adopting a configuration in which, as described above, the amount of ions generated and emitted by the ion generating section is less when the image forming apparatus is operating than when the image forming apparatus is in standby, from a different perspective than in the scheme stated above, ions can be efficiently emitted in the image forming apparatus.

In the above image forming apparatus in which the amount of ions generated and emitted by the ion generating section is less when the image forming apparatus is operating than when the image forming apparatus is in standby, the ion generating section may be configured in the following manner.

That is, the ion emission direction is made switchable between a direction towards the main body of the image forming apparatus and a direction other than towards the main body. The ion emission direction is set to the direction towards the main body when the image forming apparatus is operating, and the ion emission direction is set to the direction other than towards the main body when the image forming apparatus is in standby.

By setting the ion emission direction to the direction towards the main body of the image forming apparatus as described above, it is possible to more effectively cover the surroundings of the image forming apparatus with air including ions in the manner of an air curtain, as described above. Accordingly, by adopting such a configuration, it is possible to more reliably purify harmful exhaust gas discharged from the image forming apparatus.

When setting the ion emission direction to the direction other than towards the main body of the image forming apparatus, for example, the ion emission direction is set upward such that emission of ions is directed higher in the room. By adopting such a configuration, ions flow and are scattered throughout the room, purifying air in a wide range, so air within the room can be efficiently purified.

Accordingly, as described above, by making the ion emission direction switchable between a direction towards the main body of the image forming apparatus and a direction other than towards the main body, the above purification of air in the room by ions when the image forming apparatus is in standby, and the above purification of harmful exhaust gas discharged from the image forming apparatus by ions when the image forming apparatus is operating, can both be performed efficiently.

In the above image forming apparatus in which the emission direction of ions generated and emitted by the ion generating section is made switchable between a direction towards the main body of the image forming apparatus and the direction other than towards the main body, the ion generating section may be configured in the following manner.

That is, the ion generating section includes a swiveling mechanism, and the ion emission direction is switched between the direction towards the main body of the image forming apparatus and the direction other than towards the main body by the swiveling mechanism.

By adopting this sort of configuration, the configuration of the ion generating section in the image forming apparatus can be made simple.

Alternatively, a movable wall may be provided within the ion generating section, and the ion emission direction switched between the direction towards the main body of the image forming apparatus and the direction other than towards the main body by changing the position of the movable wall.

By adopting such a configuration, it is not necessary for the entire ion generating section to be movable, such as in the above configuration in which a swiveling mechanism is provided, so the ion generating section can be attached in an immovably fixed manner.

In the above image forming apparatus, ordinarily the following sort of configuration is adopted. That is, changing from standby to operation of the image forming apparatus is performed due to generation of a signal that instructs the image forming apparatus to start the image forming processing, by a manual operation of the image forming apparatus or by transmission from an external apparatus connected to the image forming apparatus.

Also, in the above image forming apparatus, the ion generating section may simultaneously generate and emit positive ions and negative ions as the ions. It is known that by adopting such a configuration, airborne bacteria in the air can be effectively removed.

BRIEF DESCRIPTION OF THE DRAWINGS

FIG. 7 is a perspective view that shows a state in which an ion generating apparatus is attached in Embodiment 3.

FIG. 8 is a perspective view that shows a state in which the ion generating apparatus is attached in Embodiment 3.

DETAILED DESCRIPTION OF THE INVENTION

Hereinafter, an image forming apparatus in embodiments of the present invention will be described with reference to the drawings. The image forming apparatus in these embodiments is an image forming apparatus that performs processing to form an image on a recording paper, and includes, external to a main body of the image forming apparatus, an ion generating section that generates ions and emits those ions to the outside.

Therefore, in the description of the image forming apparatus in these embodiments, first the main body of the image forming apparatus will be described as an apparatus that performs processing to form an image on a recording paper, and then an ion generating apparatus provided in the image forming apparatus will be described.

In the image forming apparatus in these embodiments, the main body of the image forming apparatus is a portion that performs image forming processing in the image forming apparatus. The main body of the image forming apparatus is provided with an independent case. That is, conceptually, the main body of the image forming apparatus includes both the case of the image forming apparatus and a portion (the portion that performs image forming processing) built into this case.

Main Body of Image Forming Apparatus

Figure 1:
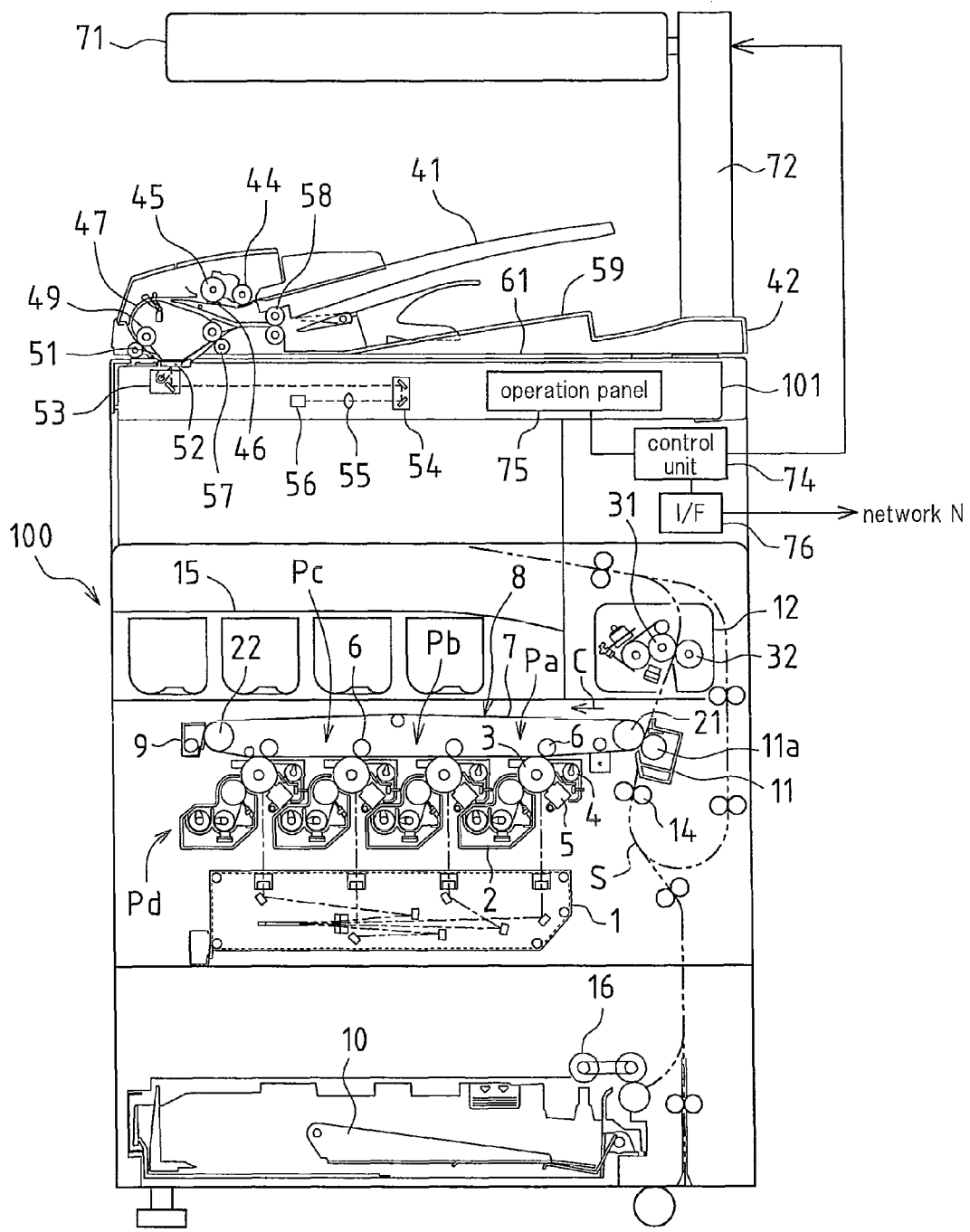
FIG. 1 is a cross-sectional view of an image forming apparatus in the present embodiments.

First, the main body of the image forming apparatus will be described as an apparatus that performs processing to form an image on a recording paper. FIG. 1 is a cross-sectional view of an image forming apparatus 100 in the present embodiment. In the present embodiment, the image forming apparatus 100 refers to the entire configuration including both the aforementioned main body of the image forming apparatus and an ion generating apparatus.

The image forming apparatus 100 is an apparatus that records an image of an original that has been read by an original reading apparatus 101 or an image received from outside onto a recording paper in color or monochrome.

The original reading apparatus 101 reads an image of an original conveyed by an original conveying unit 42. In the original conveying unit 42, when an original is placed in an original placement tray 41, an original pickup roller 44 rotates while pressing against the surface of the original, and the original is pulled out from the original placement tray 41, passed between a separation roller 45 and a separation pad 46 and separated sheet-by-sheet, and then conveyed to a conveying path 47.

In the conveying path 47, the leading edge of the original contacts an original registration roller 49, the leading edge of the original is aligned parallel to the original registration roller 49, and then the original is conveyed by the original registration roller 49 and passes between a reading guide 51 and a reading glass 52. Furthermore, the original is conveyed by a conveying roller 57, and discharged to a discharge tray 59 via a discharge roller 58.

In the original reading apparatus 101, when the original passes between the reading guide 51 and the reading glass 52, light of a light source of a first scanning unit 53 is irradiated on the surface of the original via the reading glass 52, that reflected light is incident on the first scanning unit 53 via the reading glass 52, that reflected light is reflected by a mirror of the first scanning unit 53 and a second scanning unit 54 and guided to an imaging lens 55, and an image of the original is formed on a CCD (Charge Coupled Device) 56 by the imaging lens 55. The CCD 56 reads the image of the original, and outputs image data that expresses the image of the original.

It is also possible to read an original that has been placed on an original placement glass 61. The original conveying unit 42 is pivotably supported so as to be capable of opening/closing at the rear face side of the original reading apparatus 101, and when the original conveying unit 42 is opened, the original placement glass 61 is released, so that an original can be placed on the original placement glass 61. When an original is placed on the original placement glass 61 and the original conveying unit 42 closed, while the first scanning unit 53 and the second scanning unit 54 are moved in a sub-scanning direction, the surface of the original on the original placement glass 61 is exposed to light by the first scanning unit 53, reflected light from the surface of the original is guided to the imaging lens 55 by the first scanning unit 53 and the second scanning unit 54, and an image of the original is formed on the CCD 56 by the imaging lens 55. At this time, the first scanning unit 53 and the second scanning unit 54 are moved while maintaining a predetermined speed relative to each other, so that the positional relationship of the first scanning unit 53 and the second scanning unit 54 is always maintained such that there is no change in the length of the light path of the reflected light, that is, the path of original surface→the first scanning unit 53 and the second scanning unit 54→the imaging lens 55→CCD 56. Thus, focus of the image of the original on the CCD 56 is always accurately maintained.

The entire image of the original that has thus been read is transported to and received by a laser exposing apparatus 1 of the image forming apparatus 100 as image data, and the image is recorded to a recording paper in the image forming apparatus 100.

On the other hand, the image forming apparatus 100 includes the laser exposing apparatus 1, a development apparatus 2, a photosensitive drum 3, a charging unit 5, a cleaning apparatus 4, an intermediate transfer belt apparatus 8, a fixing apparatus 12, a paper conveying path S, a paper supply tray 10, a paper discharge tray 15, and so forth.

The image data handled by the image forming apparatus 100 corresponds to a color image employing each of the colors black (K), cyan (C), magenta (M), and yellow (Y), or corresponds to a monochrome image employing a single color (for example, black). Accordingly, four each of the development apparatus 2, the photosensitive drum 3, the charging unit 5, and the cleaning apparatus 4 are provided so as to form latent images of four types corresponding to the respective colors, with the four respectively being associated with black, cyan, magenta and yellow, thus constituting four image stations Pa, Pb, Pc, and Pd.

The photosensitive drum is disposed in approximately the center of the image forming apparatus 100.

The charging unit 5 is a charging means for uniformly charging the surface of the photosensitive drum 3 to a predetermined potential. A contact-type (roller-type or brush-type) charging unit or a charger-type charging unit is used for the charging unit 5.

The laser exposing apparatus 1 is a laser scanning unit (LSU) provided with a laser diode and a reflecting mirror, and exposes the charged surface of the photosensitive drum 3 according to the image data to form an electrostatic latent image that corresponds to the image data on that surface.

The development apparatus 2 develops the electrostatic latent image formed on the photosensitive drum 3 using toner (of the colors C, M, Y, K). The cleaning apparatus 4 removes and recovers toner remaining on the surface of the photosensitive drum 3 after development and image transfer.

The intermediate transfer belt apparatus 8, disposed above the photosensitive drum 3, includes an intermediate transfer belt 7, an intermediate transfer belt drive roller 21, a driven roller 22, an intermediate transfer roller 6, an intermediate transfer belt cleaning apparatus 9.

The intermediate transfer belt 7 is supported stretched across the intermediate transfer belt drive roller 21, the intermediate transfer roller 6, the driven roller 22, and so forth, which cause the intermediate transfer belt 7 to revolve in the direction of arrow C.

The intermediate transfer roller 6 is rotatably supported near the intermediate transfer belt 7, and is pressed against the photosensitive drum 3 via the intermediate transfer belt 7. A transfer bias for transferring a toner image of the photosensitive drum 3 to the intermediate transfer belt 7 is applied to the intermediate transfer roller 6.

The intermediate transfer belt 7 is provided so as to contact each photosensitive drum 3, and by transferring the toner image on the surface of each photosensitive drum 3 to the intermediate transfer belt 7 by sequentially stacking these images, a color toner image (a toner image including each color) is formed. This transfer belt is formed as an endless belt employing a film having a thickness of about 100 to 150 μm.

The transfer of the toner image from the photosensitive drum 3 to the intermediate transfer belt 7 is performed by the intermediate transfer roller 6 pressing against the back face of the intermediate transfer belt 7. A high voltage transfer bias (a high voltage of opposite polarity (+) as the toner charging polarity (−)) for transferring the toner image is applied to the intermediate transfer roller 6. The intermediate transfer roller 6 is a roller that has a metal (for example, stainless steel) shaft with a diameter of 8 to 10 mm as a base, the surface of that shaft being covered by a conductive elastic material (for example, EPDM, urethane foam, or the like). With this conductive elastic material, it is possible to uniformly apply a high voltage to a recording paper.

As described above, the toner images on the surface of each photosensitive drum 3 are stacked on the intermediate transfer belt 7 to become a color toner image expressed by image data. The toner images of the respective colors that have been stacked in this way are conveyed along with the intermediate transfer belt 7, and transferred onto the recording paper by a transfer roller 11a of a secondary transfer apparatus 11 that contacts the intermediate transfer belt 7.

The intermediate transfer belt 7 and the transfer roller 11a of the secondary transfer apparatus 11 are put in contact with each other to form a nip region. Also, a voltage (a high voltage of opposite polarity (+) as the toner charging polarity (−)) for transferring the toner images of each color on the intermediate transfer belt 7 to the recording paper is applied to the transfer roller 11a of the secondary transfer apparatus 11. Furthermore, in order to steadily obtain that nip region, a hard material (such as a metal) is adopted for either the transfer roller 11a of the secondary transfer apparatus 11 or the intermediate transfer belt drive roller 21, and a soft material (such an elastic rubber roller or a foam resin roller) such as an elastic roller is adopted for the other.

Toner may remain on the intermediate transfer belt 7, without the toner image on the intermediate transfer belt 7 being completely transferred onto the recording paper by the secondary transfer apparatus 11. This remaining toner causes toner color mixing to occur in a subsequent process. Therefore, the remaining toner is removed and recovered by the intermediate transfer belt cleaning apparatus 9. In the intermediate transfer belt cleaning apparatus 9, for example as a cleaning member, a cleaning blade is provided that contacts the intermediate transfer belt 7 and removes the remaining toner. The back side of the intermediate transfer belt 7 is supported by the driven roller 22 at the location where the cleaning blade makes contact.

The paper supply tray 10 stores recording paper, is provided below the image forming unit of the image forming apparatus 100, and supplies recording paper in the tray.

An S-shaped paper conveying path S for feeding recording paper that has been supplied from the paper supply tray 10 to the paper discharge tray 15 via the secondary transfer apparatus 11 and the fixing apparatus 12 is provided in the image forming apparatus 100. A paper pickup roller 16, a paper registration roller 14, the fixing apparatus 12, conveying rollers that convey the recording paper, and the like are disposed along the paper conveying path S.

The paper pickup roller 16 is provided at an end of the paper supply tray 10, and supplies the recording paper page-by-page from the paper supply tray 10 to the paper conveying path S. The conveying rollers are small rollers for promoting and assisting conveyance of the recording paper, and a plurality of the conveying rollers are provided.

The paper registration roller 14 temporarily halts recording paper that has been conveyed, aligns the leading edge of the recording paper, and conveys the recording paper in a timely manner in coordination with rotation of the photosensitive drum 3 and the intermediate transfer belt 7, such that the color toner image on the intermediate transfer belt 7 is transferred to the recording paper in the nip region between the intermediate transfer belt 7 and the transfer roller 11a of the secondary transfer apparatus 11.

For example, the paper registration roller 14, based on the detection output of an unshown pre-registration detection switch, conveys the recording paper such that the leading edge of the color toner image on the intermediate transfer belt 7 matches the leading edge of the image forming region of the recording paper in the nip region between the intermediate transfer belt 7 and the transfer roller 11a of the secondary transfer apparatus 11.

The fixing apparatus 12 is provided with a heat roller 31, a pressure roller 32, and so forth. The heat roller 31 and the pressure roller 32 sandwich and convey recording paper that has passed through the nip region between the intermediate transfer belt 7 and the transfer roller 11a of the secondary transfer apparatus 11.

The heat roller 31 is controlled based on the detection output of an unshown temperature detector to become a predetermined fixing temperature, and has a function of, by applying heat and pressure together with the pressure roller 32 to the recording paper, melting, mixing, and applying pressure to the toner image that has been transferred to the recording paper, thus hot-fixing that toner image on the recording paper.

After the toner images of each color have been fixed, the recording paper is discharged face-down on the paper discharge tray 15 by the conveying rollers.

Ion Generating Apparatus

As described above, the image forming apparatus 100 in the present embodiment is provided with an ion generating apparatus 71 external to the main body of the image forming apparatus 100, that is, external to the case of the image forming apparatus. The ion generating apparatus 71 generates ions and emits those ions to the outside. Following is a description of the ion generating apparatus 71.

The state of the above image forming apparatus 100 is ordinarily divided into a state of operation in which processing to form an image on recording paper is performed, and a standby state in which this image forming processing is not performed. Operation of the ion generating apparatus 71 differs somewhat between the operating state and the standby state.

In the present embodiments, depending on the structure and operation of the ion generating apparatus, four types of ion generating apparatuses 71A to 71D are configured in Embodiments 1 to 4, as shown in FIGS. 2 to 15. These will be described in order below. In Embodiments 1 to 4, the main body of the image forming apparatus 100 described above is used as the main body of an image forming apparatus 100 serving as an apparatus that performs processing to form an image on a recording paper. Also, the ion generating apparatus 71 and a support column 72 shown in FIG. 1 are representative of an ion generating apparatus and a support column in Embodiments 1 to 4.

Ion Generating Apparatus In Embodiment 1

Figure 2:
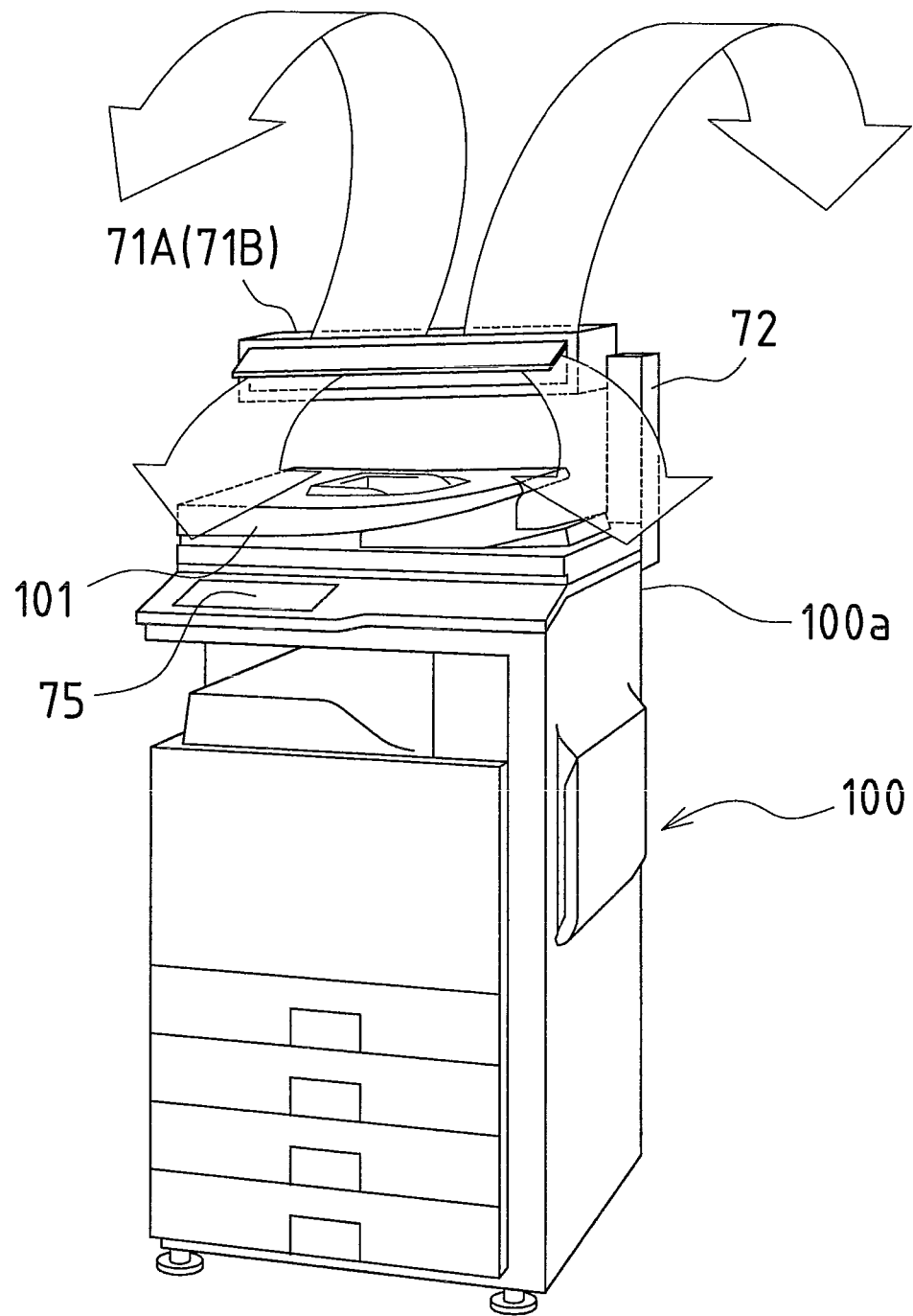
FIG. 2 is a perspective view that shows a state in which an ion generating apparatus is attached in Embodiment 1.
Figure 3:
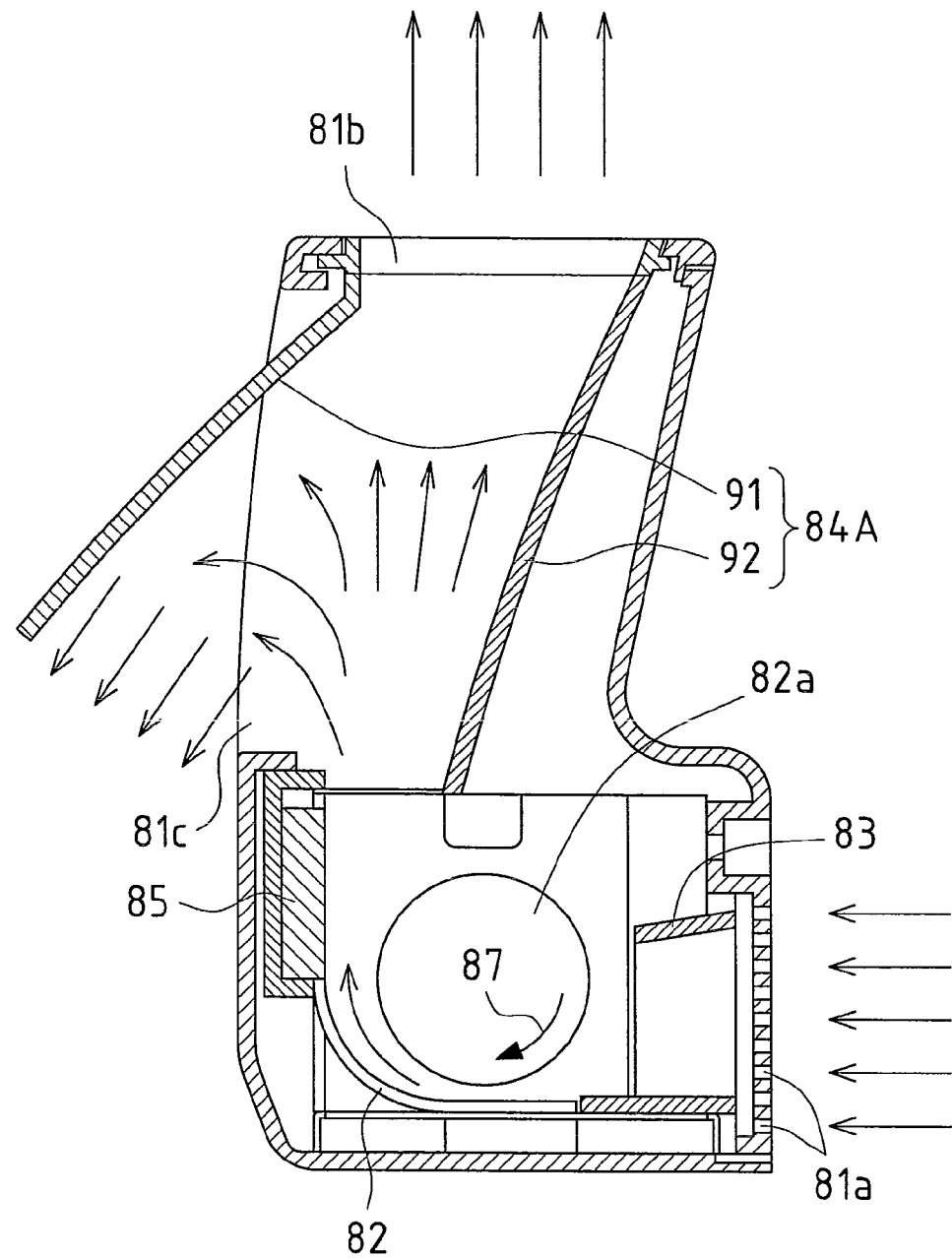
FIG. 3 is a cross-sectional view that shows the structure of the ion generating apparatus in Embodiment 1.
Figure 4:
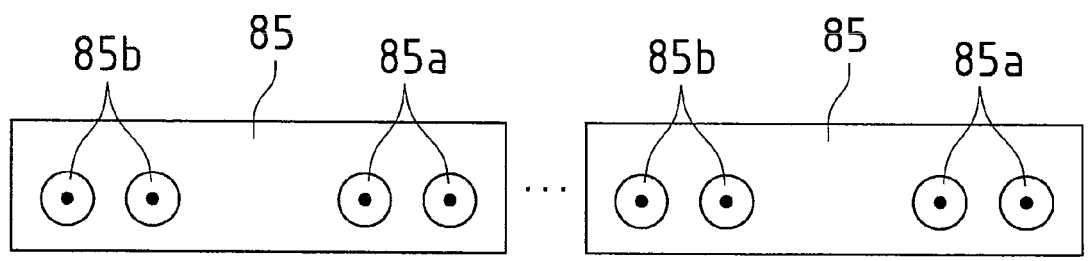
FIG. 4 is a plan view of ion generating elements built into the ion generating apparatus in Embodiment 1.
Figure 5:
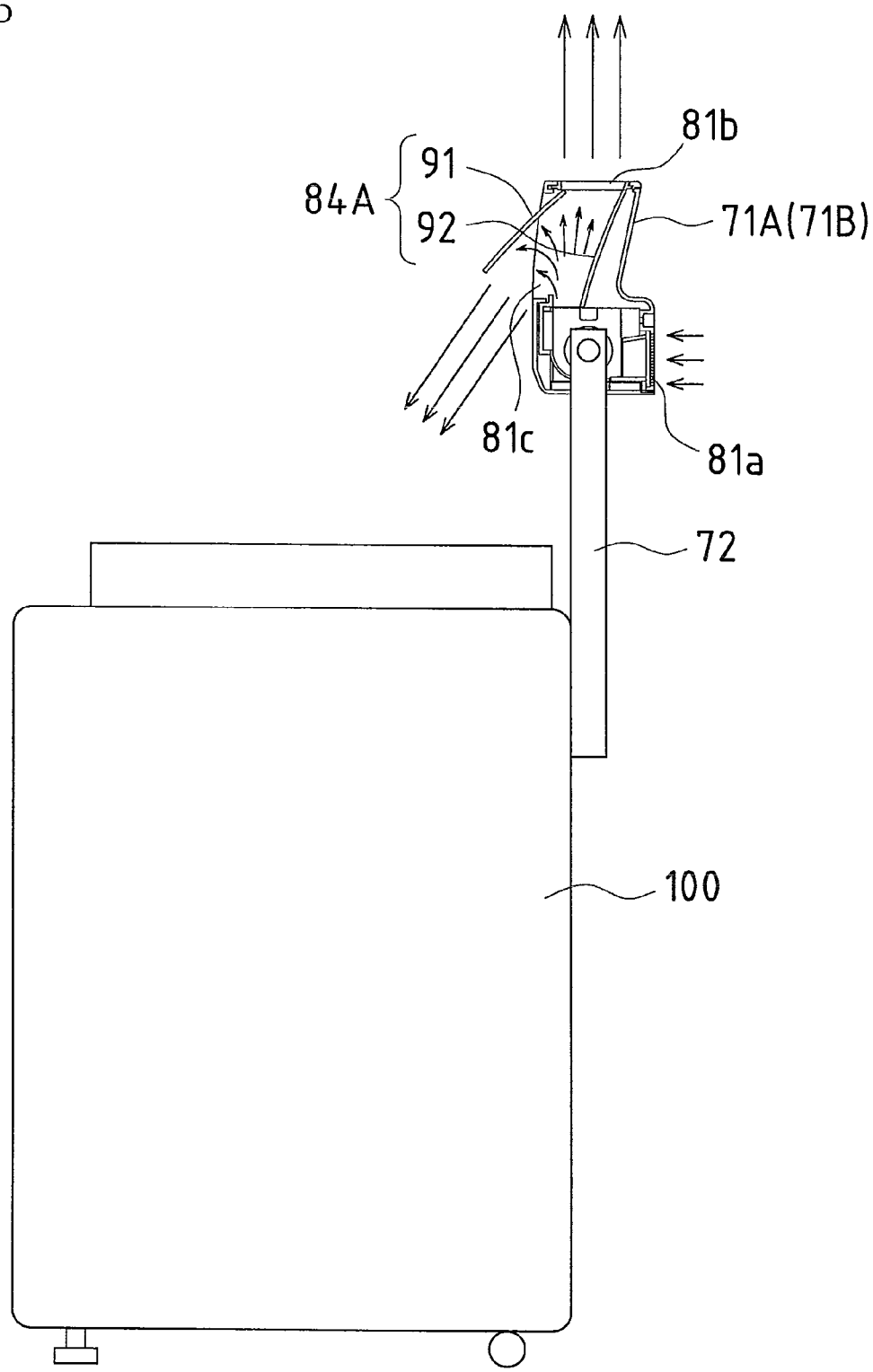
FIG. 5 is a cross-sectional view that shows an operating state of the ion generating apparatus in Embodiment 1.

Next is a description of an ion generating apparatus 71A in Embodiment 1. FIG. 2 is a perspective view that shows a state in which the ion generating apparatus 71A in Embodiment 1 has been attached to the case of the image forming apparatus 100. FIG. 3 is a cross-sectional view that shows the structure of this ion generating apparatus 71A. FIG. 4 is a plan view of ion generating elements 85 built into the ion generating apparatus 71A, and FIG. 5 is a cross-sectional view that shows an operating state of the ion generating apparatus 71A. The band-like arrows and the line arrows in the drawings indicate the direction of air flow.

Figure 16:
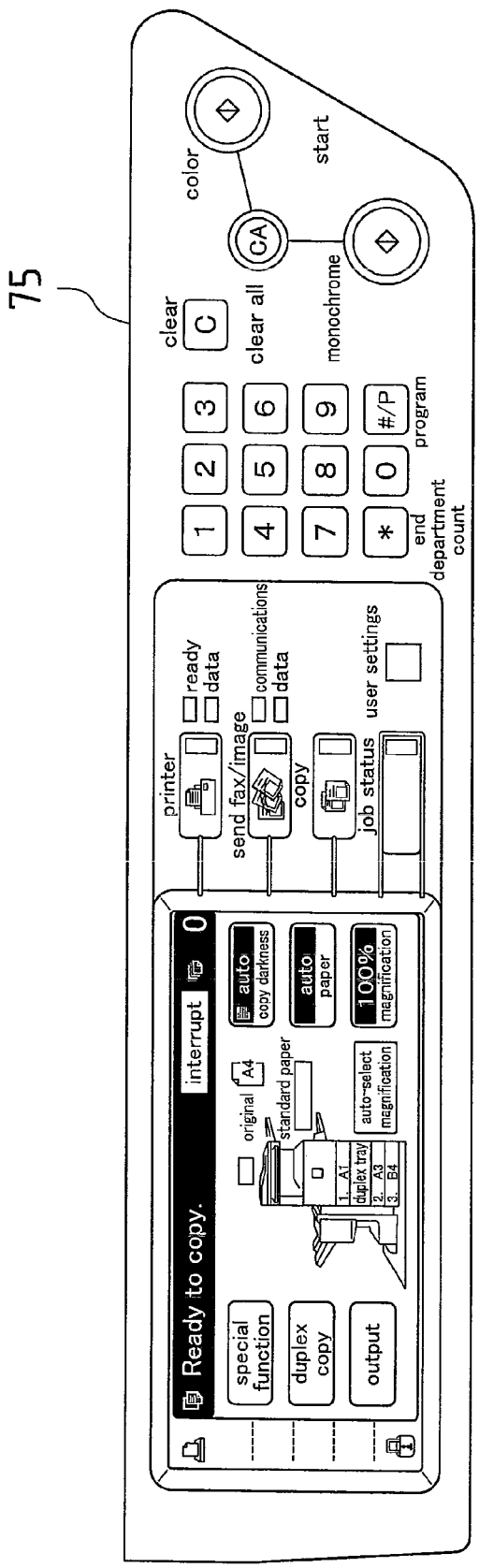
FIG. 16 is a plan view of an operating panel used in the image forming apparatus in these embodiments.

Also, as shown in FIG. 2, an operating panel 75 where an operation is performed to instruct the start of image forming processing in the image forming apparatus 100 is provided in the image forming apparatus 100. FIG. 16 is a plan view that shows the operating panel 75.

In the case of the image forming apparatus 100, the side where the operating panel 75 is provided is referred to as the front face of the case of the image forming apparatus 100, and the face on the opposite side as the front face is referred to as a rear face of the case of the image forming apparatus 100. An operator who operates the image forming apparatus 100 performs this operation from the front face side of the case of the image forming apparatus 100. This is the same in Embodiments 2 to 4 described below.

As shown in FIG. 2, the ion generating apparatus 71A in Embodiment 1 is provided external to the case of the image forming apparatus 100. Specifically, the ion generating apparatus 71A is attached to the case of the image forming apparatus 100 via the support column 72, which is provided protruding upward from a corner portion 100a on the upper side of the rear face of the case of the image forming apparatus 100. That is, the ion generating apparatus 71A is attached to the case of the image forming apparatus 100 while spaced-apart from the image forming apparatus 100.

By attaching the ion generating apparatus 71A to the case of the image forming apparatus 100 by the support column 72 in this way, the ion generating apparatus 71A can easily be provided external to the case of the image forming apparatus 100. Also, the space necessary for operating the image forming apparatus 100 can be adequately secured, so that a configuration can be adopted whereby operability of the image forming apparatus 100 is not impaired.

As shown in FIG. 2, the above-described ion generating apparatus 71A is attached perpendicular to the support column 72, has a shape elongated in the horizontal direction, and a base end of the ion generating apparatus 71A is supported at the tip end of the support column 72. The ion generating apparatus 71A is immovably attached to the support column 72. Also, the longitudinal direction of the ion generating apparatus 71A intersects the front-rear direction of the case of the image forming apparatus 100 perpendicularly in the horizontal plane.

As shown in FIG. 3, the ion generating apparatus 71A has a cross-sectional shape that is approximately L-shaped, bending in the rear face direction. Note that in FIG. 3, the left side when facing the drawing is the front face side of the ion generating apparatus 71A, and the right side when facing the drawing is the rear face side of the ion generating apparatus 71A.

The above ion generating apparatus 71A is configured as follows. First, a fan unit 82 in which a fan 82a is mounted is built into the ion generating apparatus 71A in the lower portion within the ion generating apparatus 71A. A plurality of intake holes 81a are formed in the rear face of the lower portion of the ion generating apparatus 71A, an upper face outlet 81b is formed in the upper face of the ion generating apparatus 71A, and a front face outlet 81c is formed in the upper portion of the front face of the ion generating apparatus 71A.

An intake duct 83 that guides air drawn in via the intake holes 81a to the fan unit 82 is formed between the intake holes 81a and the fan unit 82. An outlet duct 84A that guides air delivered from the fan unit 82 to the upper face outlet 81b and the front face outlet 81c is formed between the fan unit 82 and the upper face outlet 81b and the front face outlet 81c.

The outlet duct 84A is provided with a fixed duct front wall 91 and a fixed duct rear wall 92. The fixed duct front wall 91 extends from the front edge of the upper face outlet 81b diagonally downward in front of the front face outlet 81c, and has a plate-like shape that bulges slightly to the top side. The fixed duct rear wall 92 extends from the center portion of the upper face of the fan unit 82 to the rear edge of the upper face outlet 81b, and has a plate-like shape that bulges slightly to the front face side.

Ion generating elements 85 are provided on the front face side of the fan unit 82 in the lower portion within the ion generating apparatus 71A. The ion generating elements 85 are configured with Plasmacluster Ion (registered trademark) generating elements (PCI). As shown in FIG. 4, a plurality of these ion generating elements 85 are arranged in the longitudinal direction of the ion generating apparatus 71A.

As shown in FIG. 4, each ion generating elements 85 includes a pair of positive ion generating elements 85a that generate positive ions and a pair of negative ion generating elements 85b that generate negative ions. Using these positive ion generating elements 85a and negative ion generating elements 85b, it is possible to simultaneously generate positive ions and negative ions.

It is known to effectively remove airborne bacteria in the air by simultaneously generating positive ions and negative ions in this way. The ion generating elements 85 are described in detail in JP 2002-58731A, having the same applicant as the present invention.

The above fan 82a and ion generating elements 85 are connected to a control unit 74 of the image forming apparatus 100 shown in FIG. 1, and the fan 82a and the ion generating elements 85 are controlled by this control unit 74. With this control, an increase or decrease in the amount of ions emitted from the ion generating apparatus 71A is controlled.

Control of the increase or decrease in the amount of ions emitted from the ion generating apparatus 71A is performed by two methods. In the first control method, the increase or decrease in the amount of ions emitted from the ion generating apparatus 71A is controlled by increasing or decreasing the air volume from the fan 82a. The increase or decrease in the air volume from the fan 82a is performed by increasing or decreasing revolutions of the fan 82a. In the second control method, the increase or decrease in the amount of ions emitted from the ion generating apparatus 71A is controlled by increasing or decreasing the number of ion generating elements 85 caused to operate.

By adopting such a configuration, it is possible to easily and reliably vary the amount of ions generated and emitted by the ion generating apparatus 71A.

As shown in FIG. 3, in the above ion generating apparatus 71A, with regard to air that has been drawn in via the intake holes 81a due to the fan 82a mounted in the fan unit 82 rotating in the direction of arrow 87 indicating the rotation direction, positive ions and negative ions generated by the ion generating elements 85 are included in this air via the fan unit 82, and the air is emitted to outside from the upper face outlet 81b and the front face outlet 81c.

Among this air, air emitted from the upper face outlet 81b is emitted upward and scattered. Accordingly, air emitted from the upper face outlet 81b is scattered in the room in which the image forming apparatus 100 is installed.

On the other hand, because the fixed duct front wall 91 of the outlet duct 84A extends from the front edge of the upper face outlet 81b diagonally downward in front of the front face outlet 81c, air emitted from the front face outlet 81c is emitted diagonally downward in front of the front face outlet 81c and scattered. This direction diagonally downward to the front leads to the upper portion of the case of the image forming apparatus 100. Accordingly, air emitted from the front face outlet 81c is scattered around the case of the image forming apparatus 100.

The ion generating apparatus 71A configured as described above operates in the following manner during operation to perform processing to form an image on recording paper in the image forming apparatus 100, and during standby in which this image forming processing is not performed.

That is, a configuration is adopted in which the amount of ions generated and emitted by the ion generating apparatus 71A is less during standby than during operation in the image formatting apparatus 100. As described above, control of this increase or decrease in the amount of ions is performed by the control unit 74 of the image forming apparatus shown in FIG. 1. As for the content of this control, either the above first control method or the above second control method is performed, or both control methods are performed simultaneously.

This control is performed based on the state of the image forming apparatus 100, and changing from standby to operation of the image forming apparatus 100 is performed due to generation of a signal that instructs the image forming apparatus 100 to start image forming processing. Also, changing from operation to standby of the image forming apparatus 100 is performed due to image forming processing ending in the image forming apparatus 100.

Generation of a signal that instructs the image forming apparatus 100 to start image forming processing is performed by an operator using the operating panel 75 of the image forming apparatus 100 shown in FIG. 16. Alternatively, such a signal is generated by signal transmission from an external apparatus on a network N connected via an interface 76 (I/F) connected to the control unit 74 of the image forming apparatus 100 shown in FIG. 1.

In the above ion generating apparatus 71A, the reasons for adopting a configuration in which the amount of ions generated and emitted by the ion generating apparatus 71A is less during standby than during operation in the image forming apparatus 100 are as follows.

That is, during operation of the image forming apparatus 100, because the image forming apparatus 100 is operating, it is necessary to both purify the air in the room in which the image forming apparatus 100 is installed, and also purify harmful exhaust gas discharged from the case of the image forming apparatus 100. Therefore, in comparison to when the image forming apparatus 100 is in standby, many ions are emitted to the outside during operation of the image forming apparatus 100.

According to the above ion generating apparatus 71A, it is possible to provide the ion generating apparatus 71A external to the case of the image forming apparatus 100, so while suppressing increased size and cost of the image forming apparatus 100, it is possible to purify harmful exhaust gas discharged from the case of the image forming apparatus 100, and also possible to purify air in the room where the image forming apparatus 100 has been installed. That is, a single device can serve both the role of purifying exhaust gas from the case of the image forming apparatus 100, and purifying air within the room.

Also, the ion generating apparatus 71A can emit more ions to the outside during operation of the image forming apparatus 100 than during standby of the image forming apparatus 100, so it is possible to both adequately purify harmful exhaust gas discharged from the case of the image forming apparatus 100, and adequately purify air in the room where the image forming apparatus 100 has been installed.

Also, it is possible to adopt a configuration in which the amount of ions emitted by the ion generating apparatus 71A is less during standby of the image forming apparatus 100 than during operation of the image forming apparatus 100. As described above, during standby of the image forming apparatus 100 it is sufficient to only purify air in the room where the image forming apparatus 100 has been installed; it is not necessary to purify harmful exhaust gas discharged from the case of the image forming apparatus 100. Therefore, it is possible to efficiently emit ions in the image forming apparatus 100.

In the above ion generating apparatus 71A, the ion generating apparatus 71A is attached to the case of the image forming apparatus 100 via the support column 72, which is provided protruding upward from the corner portion 100a on the upper side of the rear face of the case of the image forming apparatus 100. However, this is not a limitation; the following sort of configuration may also be adopted.

Figure 6:
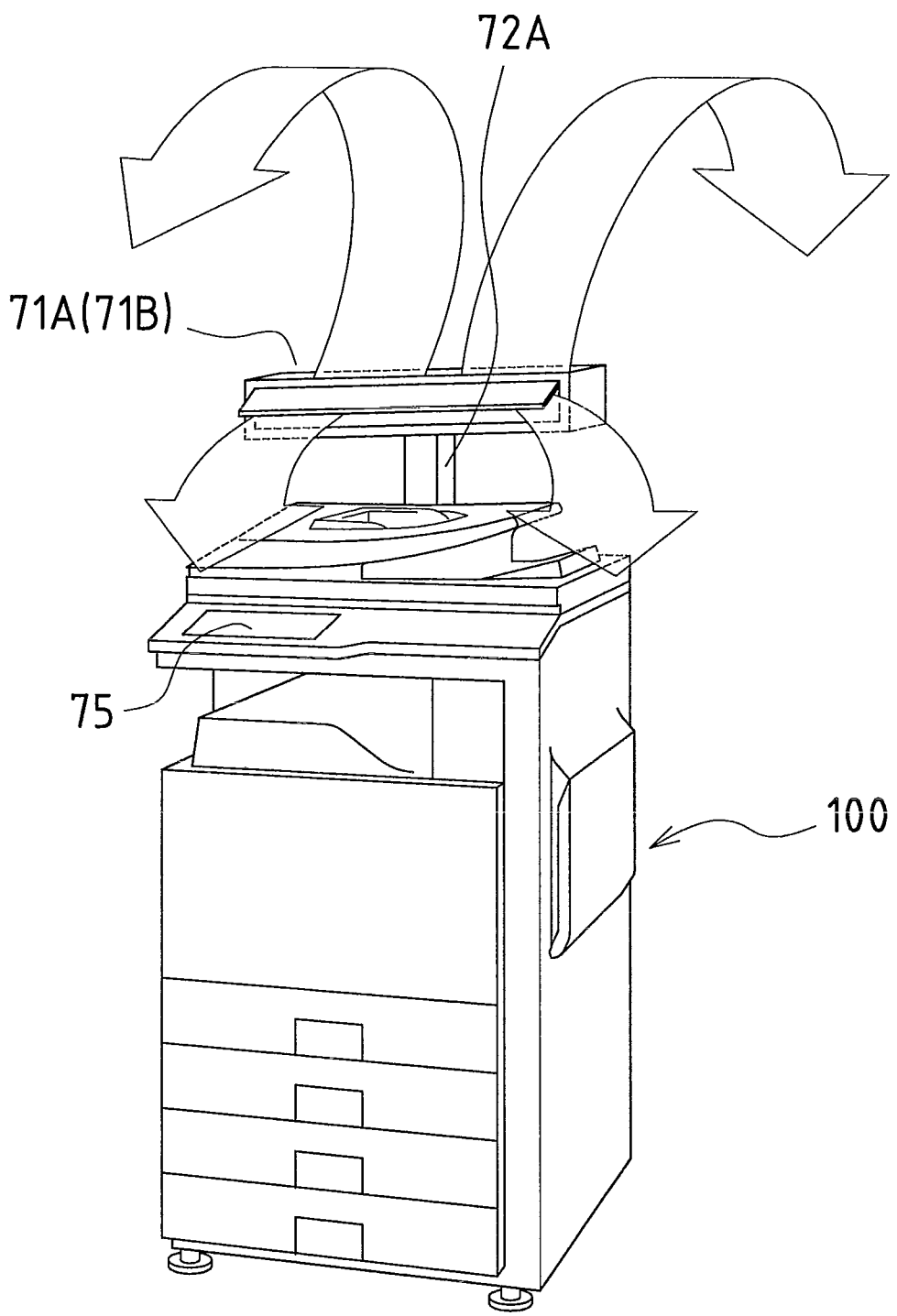
FIG. 6 is a perspective view that shows another state in which the ion generating apparatus is attached in Embodiment 1.

That is, as shown in FIG. 6, the ion generating apparatus 71A can be attached to the case of the image forming apparatus 100 via the support column 72, which is provided protruding upward from the center portion on the upper side of the rear face of the case of the image forming apparatus 100.

When such a configuration is adopted, same as when the ion generating apparatus 71A is attached to the case of the image forming apparatus 100 by the support column 72, the ion generating apparatus 71A can easily be provided external to the case of the image forming apparatus 100. Also, the space necessary for operating the image forming apparatus 100 can be adequately secured, so that a configuration can be adopted whereby operability of the image forming apparatus 100 is not impaired.

Ion Generating Apparatus In Embodiment 2

Next is a description of an ion generating apparatus 71B in Embodiment 2. The hardware configuration of the ion generating apparatus 71B in Embodiment 2, and attachment to the case of the image forming apparatus 100, are identical to those of the ion generating apparatus 71A in above Embodiment 1. The ion generating apparatus 71B in Embodiment 2 differs from the ion generating apparatus 71A in Embodiment 1 as follows.

That is, in the ion generating apparatus 71A in Embodiment 1, a configuration is adopted in which the amount of ions emitted by the ion generating apparatus 71A is less during standby of the image forming apparatus 100 than during operation of the image forming apparatus 100.

On the other hand, in the ion generating apparatus 71B in Embodiment 2, opposite to the ion generating apparatus 71A in Embodiment 1, a configuration is adopted in which the amount of ions emitted by the ion generating apparatus 71B is less during operation of the image forming apparatus 100 than during standby of the image forming apparatus 100.

In the ion generating apparatus 71B in Embodiment 2, by adopting a configuration in which the air volume from a fan is less during operation of the image forming apparatus 100 than during standby of the image forming apparatus 100, for example, it is possible to allow ions to be dispersed around the case of the image forming apparatus 100.

That is, it is possible to cover the surroundings of the case of the image forming apparatus 100 with air including ions, in the manner of an air curtain. Thus, it is possible to reliably purify harmful exhaust gas discharged from the case of the image forming apparatus 100.

Control of the above ion generating apparatus 71B, that is, control of the fan 82a and the ion generating elements 85, same as for the ion generating apparatus 71A in Embodiment 1, is performed by the control unit 74 of the image forming apparatus 100 shown in FIG. 1. As for the content of this control, as in the ion generating apparatus 71A in Embodiment 1, either the first control method or the second control method is performed, or both control methods are performed simultaneously in parallel.

The ion generating apparatus 71B in above Embodiment 2 is based on usage when the following sort of states are assumed. That is, during operation of the image forming apparatus 100, the apparatus is mainly dedicated to purification of harmful exhaust gas discharged from the case of the image forming apparatus 100, and during standby of the image forming apparatus 100, the apparatus purifies air in the room where the image forming apparatus 100 has been installed.

Ordinarily, the volume of the case of the image forming apparatus 100 is small relative to the volume of the room where the image forming apparatus 100 has been installed, so it is considered acceptable for the amount of ions necessary for purification of harmful exhaust gas discharged from the case of the image forming apparatus 100 to be less than the amount of ions necessary for purifying air within the room where the image forming apparatus 100 has been installed. Consequently, a configuration is adopted in which the amount of ions generated and emitted by the ion generating apparatus 71B is less during operation of the image forming apparatus 100 than during standby of the image forming apparatus 100.

Ordinarily, a tendency is seen for the time during which the image forming apparatus 100 is operating to be much less than the time during which the image forming apparatus 100 is in standby. Consequently, even if a configuration is adopted in which during operation of the image forming apparatus 100, the apparatus is mainly dedicated to purification of harmful exhaust gas discharged from the case of the image forming apparatus 100, and during standby of the image forming apparatus 100, the apparatus is mainly dedicated to purification of air in the room where the image forming apparatus 100 has been installed, it is conceivable that there will be substantially no adverse effects due to not effectively purifying air in the room where the image forming apparatus 100 has been installed during operation of the image forming apparatus 100. The configuration of the ion generating apparatus in Embodiment 2 is adopted from this perspective.

According to the above ion generating apparatus 71B, same as the ion generating apparatus 71A in Embodiment 1, it is possible to provide the ion generating apparatus 71B external to the case of the image forming apparatus 100, so while suppressing increased size and cost of the image forming apparatus 100, it is possible to purify harmful exhaust gas discharged from the case of the image forming apparatus 100, and also possible to purify air in the room where the image forming apparatus 100 has been installed. That is, a single device can serve both the role of purifying exhaust gas from the case of the image forming apparatus, and purifying air within the room.

Also, by adopting a configuration in which, as described above, the amount of ions generated and emitted by the ion generating apparatus 71B is less during operation of the image forming apparatus 100 than during standby of the image forming apparatus 100, from a different perspective than in the ion generating apparatus 71A in above Embodiment 1, it is possible to efficiently emit ions in the image forming apparatus 100.

Also, like the ion generating apparatus 71A, which as shown in FIG. 6, can be attached to the case of the image forming apparatus 100 via the support column 72, which is provided protruding upward from the center portion on the upper side of the rear face of the case of the image forming apparatus 100, the ion generating apparatus 71B can be attached to the case of the image forming apparatus 100 via the support column 72A.

Ion Generating Apparatus in Embodiment 3

Figure 9:
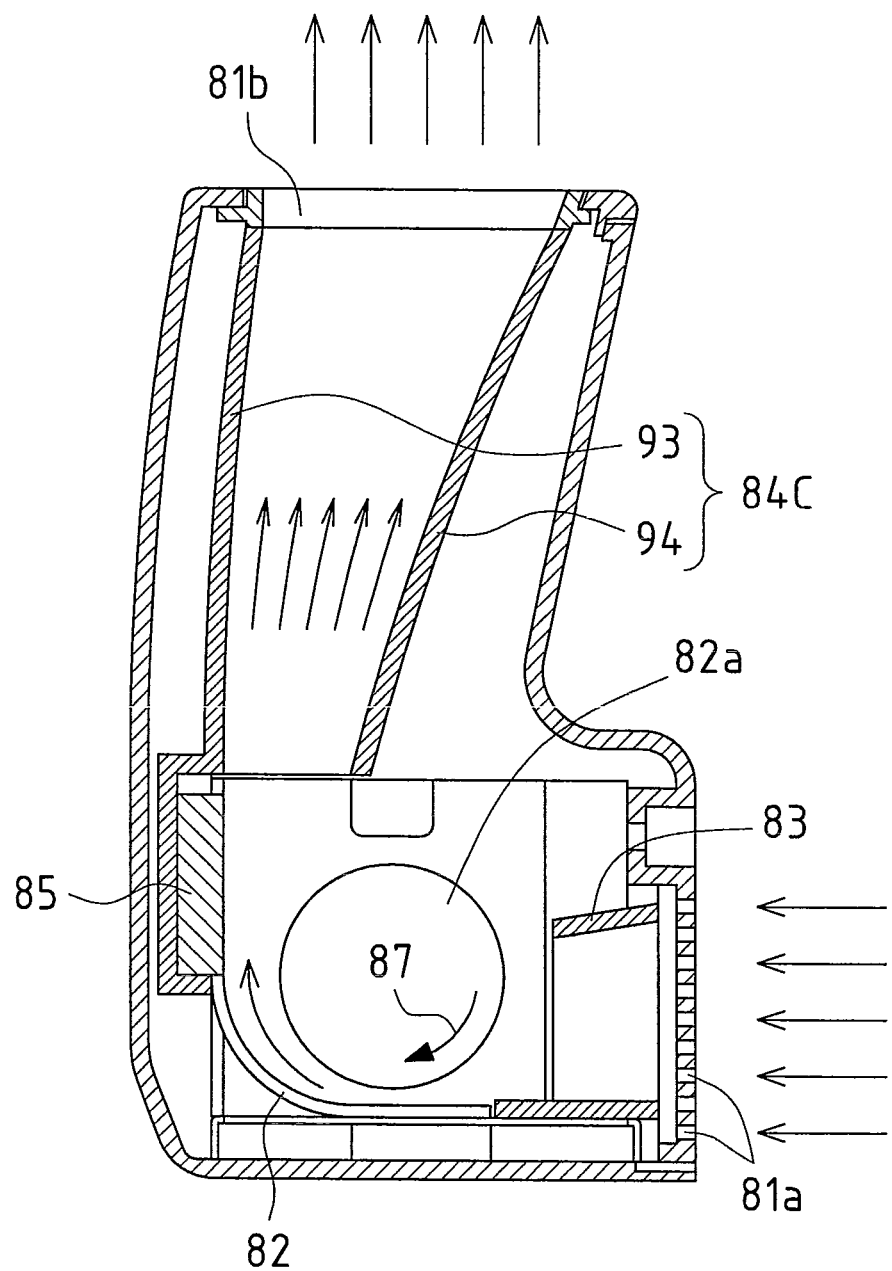
FIG. 9 is a cross-sectional view that shows the structure of an ion generating apparatus in Embodiment 3.
Figure 10:
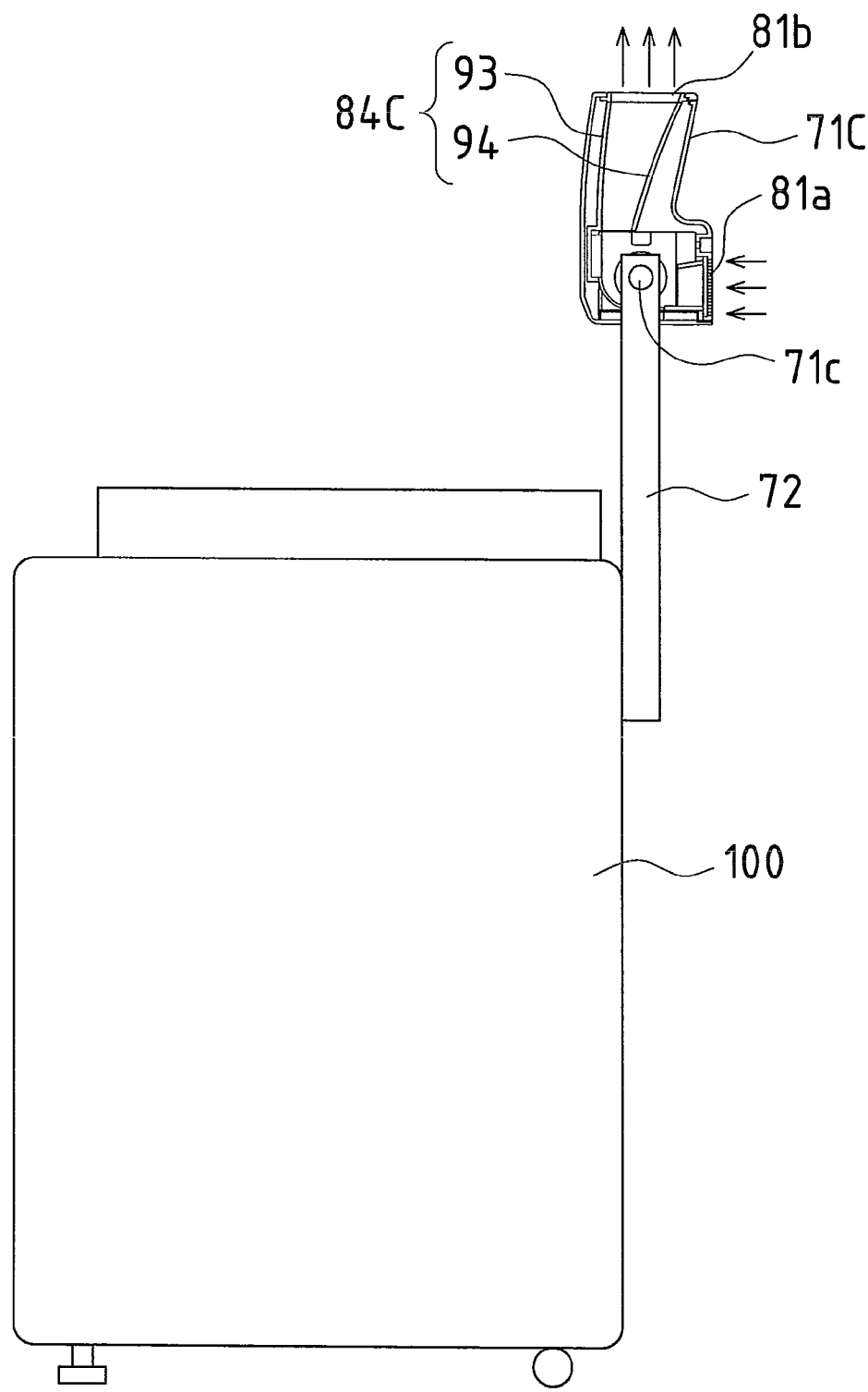
FIG. 10 is a cross-sectional view that shows an operating state of the ion generating apparatus in Embodiment 3.
Figure 11:
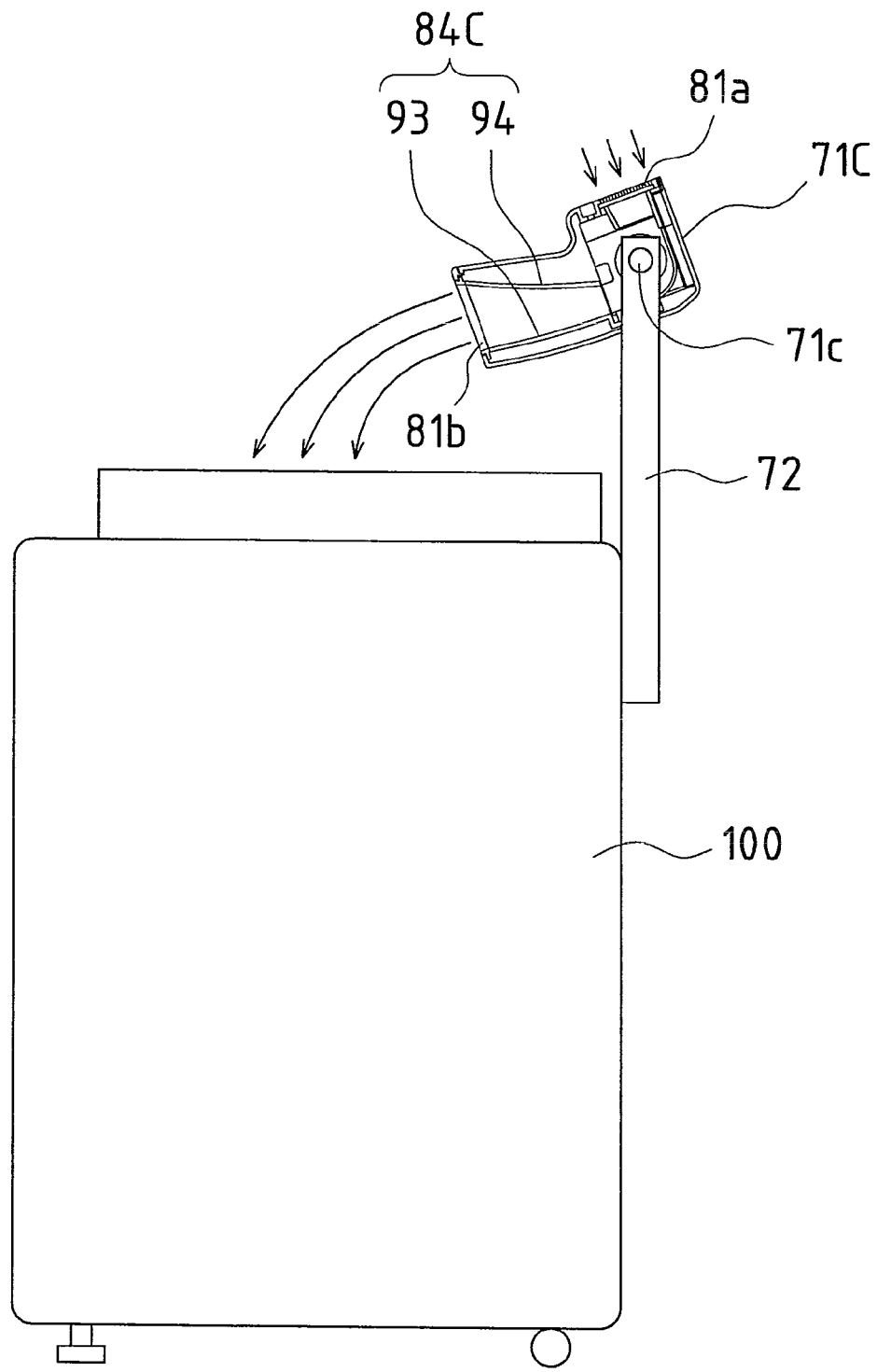
FIG. 11 is a cross-sectional view that shows an operating state of an ion generating apparatus in Embodiment 3.

Next is a description of an ion generating apparatus 71C in Embodiment 3. FIGS. 7 and 8 are perspective views that show a state in which the ion generating apparatus 71C in Embodiment 3 has been attached to the case of the image forming apparatus 100. FIG. 9 is a cross-sectional view that shows the structure of the ion generating apparatus 71C. FIG. 10 is a cross-sectional view that shows an operating state of the ion generating apparatus 71C when the image forming apparatus 100 is in standby, and FIG. 11 is a cross-sectional view that shows an operating state of the ion generating apparatus 71C when the image forming apparatus 100 is operating. The band-like arrows and the line arrows in the drawings indicate the direction of air flow.

The above ion generating apparatus 71C, like the ion generating apparatus 71B in above Embodiment 2, that is, like the ion generating apparatus 71A in above Embodiment 1, as shown in FIGS. 7 and 8, is attached to the case of the image forming apparatus 100 via the support column 72, which is provided protruding upward from the corner portion 100a on the upper side of the rear face of the case of the image forming apparatus 100. The outer appearance of the ion generating apparatus 71C also is approximately the same as that of the ion generating apparatus 71B in Embodiment 2.

The configuration of the above ion generating apparatus 71C in Embodiment 3 is approximately the same as that of the ion generating apparatus 71B in Embodiment 2, that is, approximately the same as that of the ion generating apparatus 71A in Embodiment 1. The ion generating apparatus 71C in Embodiment 3 differs from the ion generating apparatus 71B in Embodiment 2 as follows.

In the ion generating apparatus 71B in Embodiment 2, both the upper face outlet 81b in the upper face of the ion generating apparatus 71B and the front face outlet 81c in the upper portion of the front face of the ion generating apparatus 71B are formed, but in the ion generating apparatus 71C in Embodiment 3, the front face outlet 81c is not formed; as shown in FIG. 9, only the upper face outlet 81b in the upper face of the ion generating apparatus 71C is formed.

That is, an outlet duct 84C that guides air delivered from the fan unit 82 to the upper face outlet 81b is formed between the fan unit 82 and the upper face outlet 81b of the ion generating apparatus 71C.

As shown in FIG. 9, the outlet duct 84C is provided with a fixed duct front wall 93 and a fixed duct rear wall 94. The fixed duct front wall 93 extends from the front edge of the upper face of the fan unit 82 to the front edge of the upper face outlet 81b, and has a plate-like shape that bulges slightly to the front face side. The fixed duct rear wall 94 extends from the center portion of the upper face of the fan unit 82 to the rear edge of the upper face outlet 81b, and has a plate-like shape that bulges slightly to the front face side.

Also, in the ion generating apparatus 71B in Embodiment 2, the ion generating apparatus 71B is immovably attached to the support column 72, but in the ion generating apparatus 71C in Embodiment 3, as shown in FIGS. 7 and 8, and FIGS. 10 and 11, the ion generating apparatus 71C is movably attached to the support column 72. Specifically, the ion generating apparatus 71C is made able to swivel.

The movable duct rear wall 96 extends form the center portion of the upper face of the fan unit 82 to the rear edge of the upper face outlet 81b, and has a plate-like shape that bulges slightly to the front face side. A movable duct rear wall support shaft 96a is provided at the lower end of the movable duct front wall 96, and is rotatably supported in the center portion of the upper face of the fan unit 82. Arrow 98 in FIGS. 12 to 15 indicates the direction of rotation of the movable duct front wall.

Control of swiveling of the ion generating apparatus 71C is performed by the control unit 74 of the image forming apparatus 100 shown in FIG. 1.

Swiveling of the ion generating apparatus 71C, as the attitude of the ion generating apparatus 71C, is performed between a state in which the upper face outlet 81b of the ion generating apparatus 71C is directed upward, as shown in FIGS. 7 and 10, and a state in which the upper face outlet 81b is directed toward the upper face of the case of the image forming apparatus 100, as shown in FIGS. 8 and 11.

Other than the above, the above ion generating apparatus 71C is the same as the ion generating apparatus 71B in Embodiment 2, as stated above. That is, in the lower portion within the ion generating apparatus 71C, ion generating elements 85 are provided on the front face side of the fan unit 82. These ion generating elements 85 and their arrangement are identical to those in the ion generating apparatus 71B in Embodiment 2.

Also, regarding control of the above ion generating apparatus 71C, other than control of the above swiveling drive motor, control of the fan 82a and the ion generating elements 85 is the same as in the ion generating apparatus 71B in Embodiment 2, and is performed by the control unit 74 of the image forming apparatus 100 shown in FIG. 1. As for the content of this control, as in the ion generating apparatus 71B in Embodiment 2, either the first control method or the second control method is performed, or both control methods are performed simultaneously.

In the above ion generating apparatus 71C in Embodiment 3, as in the ion generating apparatus 71B in Embodiment 2, as shown in FIG. 9, due to the fan 82a mounted in the fan unit 82 rotating in the direction of arrow 87 indicating the direction of rotation, air drawn in via the intake holes 81a becomes air including positive and negative ions via the fan unit 82 and is emitted to the outside from the upper face outlet 81b.

However, in the above ion generating apparatus 71C in Embodiment 3, unlike in the ion generating apparatus 71B in Embodiment 2, the direction in which the upper face outlet 81b is pointing differs depending on the operating state of the image forming apparatus 100.

That is, when the image forming apparatus 100 is in standby, the upper face outlet 81b of the ion generating apparatus 71C is directed upward, as shown in FIGS. 7 and 10. When the image forming apparatus 100 is operating, the upper face outlet 81b is directed toward the upper face of the case of the image forming apparatus 100, as shown in FIGS. 8 and 11.

At the same time as the above, the amount of ions generated and emitted by the ion generating apparatus 71C is made less during operation of the image forming apparatus 100 than during standby of the image forming apparatus 100.

That is, when the image forming apparatus 100 is in standby, the upper face outlet 81b of the ion generating apparatus 71C is directed upwards, as shown in FIGS. 7 and 10, and also, a greater amount of ions is generated and emitted by the ion generating apparatus 71C than during operation of the image forming apparatus 100.

On the other hand, when the image forming apparatus 100 is operating, the upper face outlet 81b of the ion generating apparatus 71C is directed toward the upper face of the case of the image forming apparatus 101, as shown in FIGS. 8 and 11, and also, a smaller amount of ions is generated and emitted by the ion generating apparatus 71C than when the image forming apparatus 100 is in standby.

The reason for adopting such a configuration is that like the ion generating apparatus 71B in Embodiment 2, the ion generating apparatus 71C in Embodiment 3 also is based on usage when the following sort of states are assumed.

That is, during operation of the image forming apparatus 100, the apparatus is mainly dedicated to purification of harmful exhaust gas discharged from the case of the image forming apparatus 100, and during standby of the image forming apparatus 100, the apparatus purifies air in the room where the image forming apparatus 100 has been installed.

According to the above ion generating apparatus 71C, same as the ion generating apparatus 71B in Embodiment 2, it is possible to provide the ion generating apparatus 71C external to the case of the image forming apparatus 100, so while suppressing increased size and cost of the image forming apparatus 100, it is possible to purify harmful exhaust gas discharged from the case of the image forming apparatus 100, and also possible to purify air in the room where the image forming apparatus 100 has been installed. That is, a single device can serve both the role of purifying exhaust gas from the case of the image forming apparatus 100, and purifying air within the room.

Also, by not providing the ion generating apparatus 71B in Embodiment 2, but instead using a swivel function provided in the ion generating apparatus 71C, it is possible to achieve the same operation and effects as the ion generating apparatus 71B in Embodiment 2, to an even greater degree than with the ion generating apparatus 71B in Embodiment 2.

Note that in the above ion generating apparatus 71C, the amount of ions generated and emitted by the ion generating apparatus 71C is less when the image forming apparatus 100 is operating than when the image forming apparatus 100 is in standby, but an operating method is also possible in which the amount of ions is the same when the image forming apparatus 100 is operating and when the image forming apparatus 100 is in standby.

Regarding the attachment attitude of the above ion generating apparatus 71C, the front face outlet 81c of the ion generating apparatus 71C may be always directed toward the upper face of the case of the image forming apparatus 100, as shown in FIGS. 8 and 11. With this attitude, the amount of ions generated and emitted by the ion generating apparatus 71C may be less when the image forming apparatus 100 is operating than when the image forming apparatus 100 is in standby.

By adopting such a configuration, when the image forming apparatus 100 is in standby, air emitted from the ion generating apparatus 71C is scattered into the room where the image forming apparatus 100 is installed, and also, when the image forming apparatus 100 is operating, it is possible to allow ions to be dispersed around the case of the image forming apparatus 100, thus covering the surroundings of the case of the image forming apparatus 100, in the manner of an air curtain.

Accordingly, also when adopting the above sort of configuration, it is possible to purify air within the room, and also purify harmful exhaust gas discharged from the case of the image forming apparatus 100.

Also, like the ion generating apparatus 71B, that is, like the ion generating apparatus 71A, which as shown in FIG. 6, can be attached to the case of the image forming apparatus 100 via the support column 72, which is provided protruding upward from the center portion on the upper side of the rear face of the case of the image forming apparatus 100, the ion generating apparatus 71C can be attached to the case of the image forming apparatus 100 via the support column 72A.

In this case, a swiveling drive motor of the ion generating apparatus 71C is built into the support column 72A, and also, a function for causing the ion generating apparatus 71C to swivel is provided in the ion generating apparatus 71C and in the support column 72A.

For example, a structure can be adopted in which the ion generating apparatus 71C is divided in the center, a pivotal shaft for pivoting is provided at the end of both divided sections of the ion generating apparatus 71C on the side where these divided sections are near the support column 72A, and this pivotal shaft operates in coordination with a rotating shaft of the swiveling drive motor built into the support column.

Ion Generating Apparatus In Embodiment 4

Figure 12:
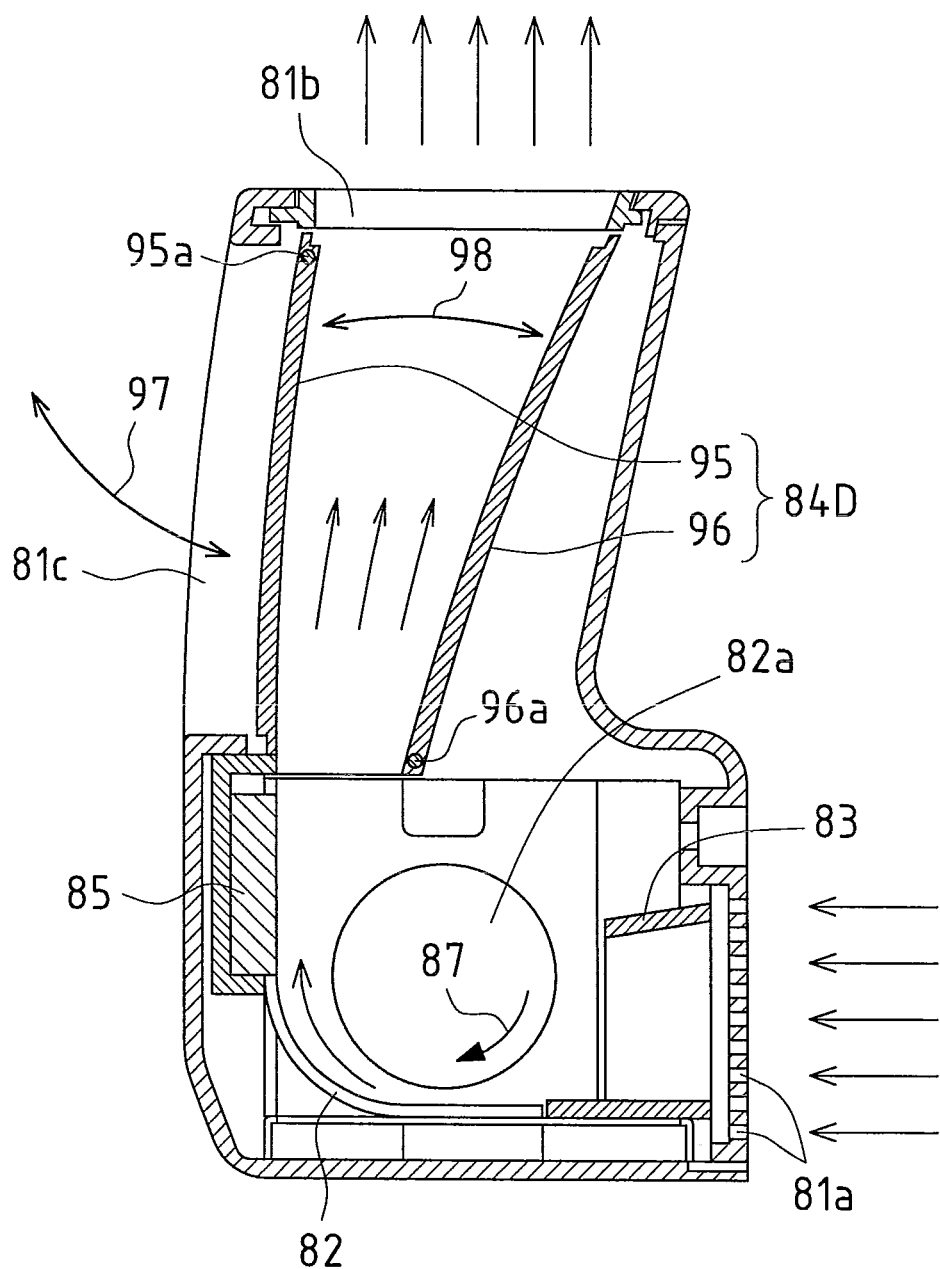
FIG. 12 is a cross-sectional view that shows the structure of an ion generating apparatus in Embodiment 4.
Figure 13:
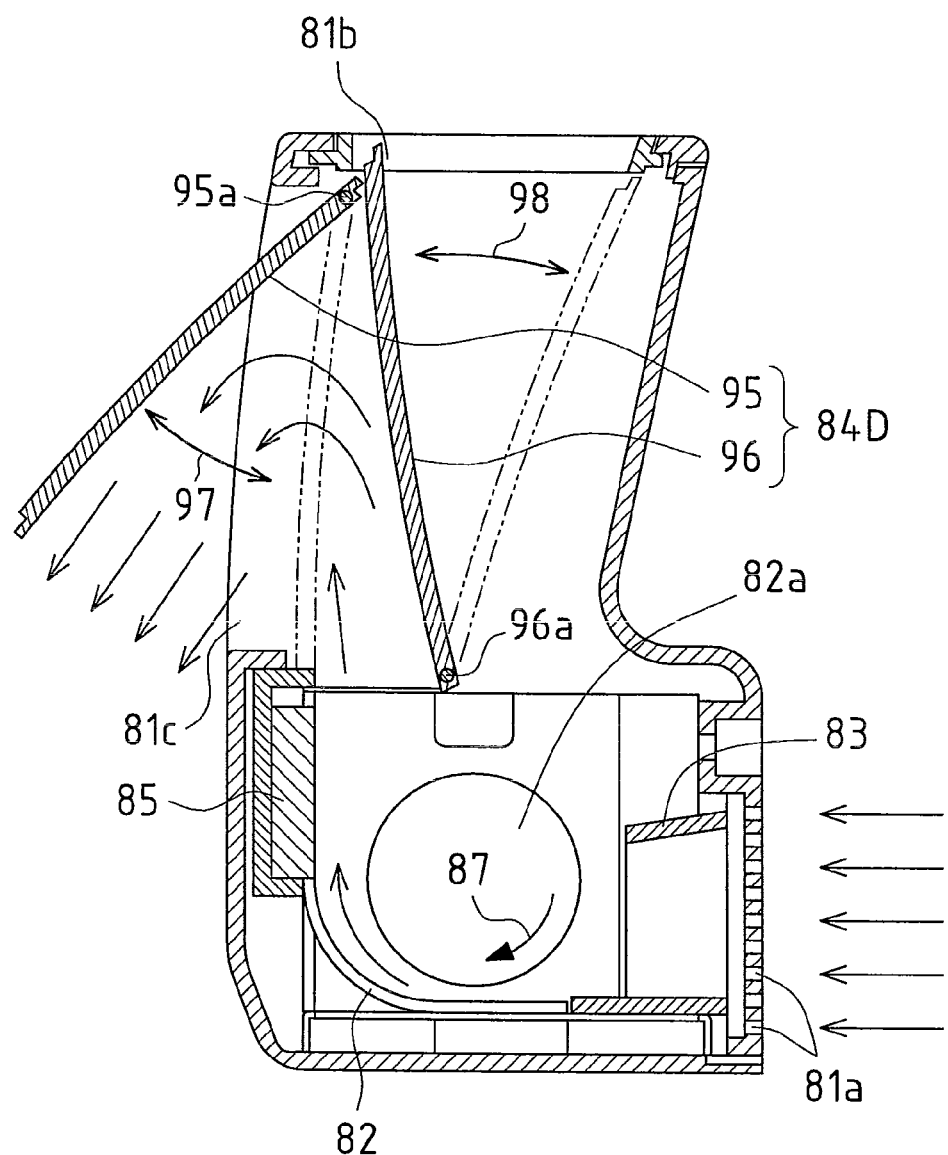
FIG. 13 is a cross-sectional view that shows the structure of the ion generating apparatus in Embodiment 4.
Figure 14:
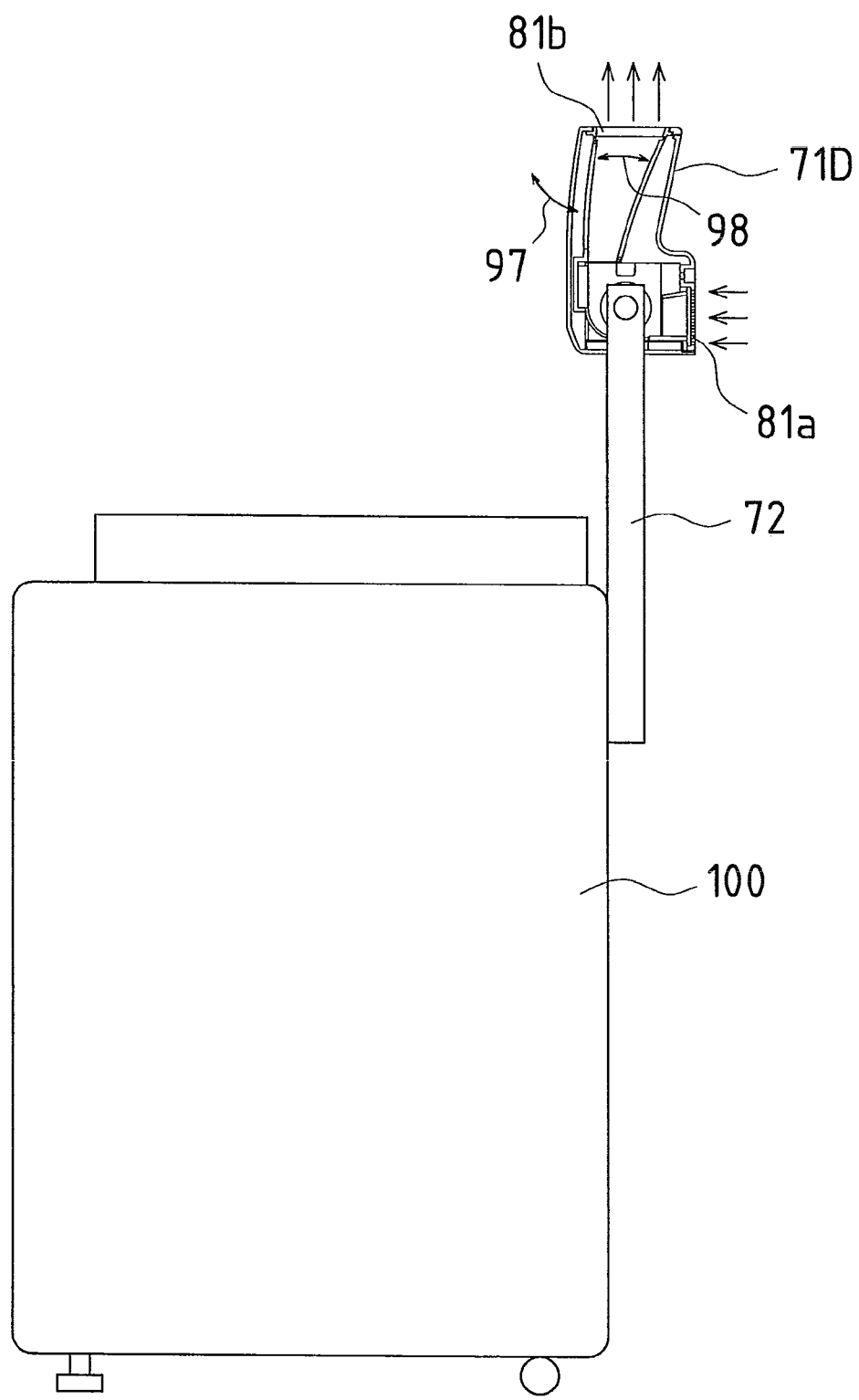
FIG. 14 is a cross-sectional view that shows an operating state of the ion generating apparatus in Embodiment 4.
Figure 15:
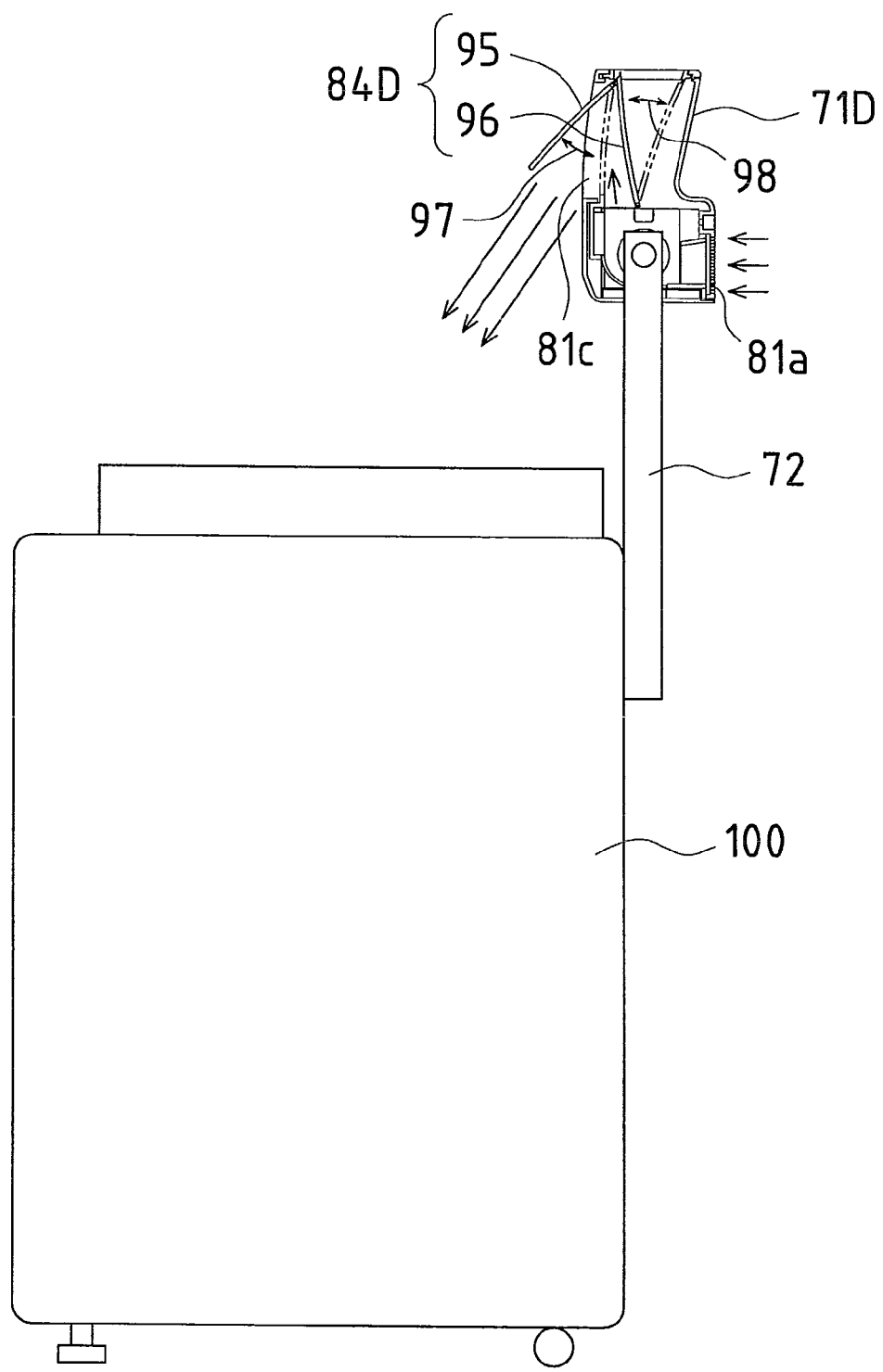
FIG. 15 is a cross-sectional view that shows an operating state of the ion generating apparatus in Embodiment 4.

Next is a description of an ion generating apparatus 71D in Embodiment 4. FIG. 12 is a cross-sectional view that shows the structure of the ion generating apparatus 71D when the image forming apparatus 100 is in standby. FIG. 13 is a cross-sectional view that shows the structure of the ion generating apparatus 71D when the image forming apparatus 100 is operating. FIG. 14 is a cross-sectional view that shows an operating state of the ion generating apparatus 71D when the image forming apparatus 100 is in standby, and FIG. 15 is a cross-sectional view that shows an operating state of the ion generating apparatus 71D when the image forming apparatus 100 is operating. The line arrows in the drawings indicate the direction of air flow.

The above ion generating apparatus 71D, like the ion generating apparatus 71C in above Embodiment 3, that is, like the ion generating apparatus 71A in above Embodiment 1, is attached to the case of the image forming apparatus 100 via the support column 72, which is provided protruding upward from the corner portion 100a on the upper side of the rear face of the case of the image forming apparatus 100. The outer appearance of the ion generating apparatus 71D also is approximately the same as that of the ion generating apparatus 71C in Embodiment 3.

The configuration of the above ion generating apparatus 71D in Embodiment 4 is approximately the same as that of the ion generating apparatus 71C in Embodiment 3. The ion generating apparatus 71D in Embodiment 4 differs from the ion generating apparatus 71C in Embodiment 3 as follows.

The ion generating apparatus 71C in Embodiment 3 is provided with a swiveling function, and by causing the ion generating apparatus 71C to swivel, when the image forming apparatus 100 is in standby, the upper face outlet 81b of the ion generating apparatus 71C is directed upward, as shown in FIG. 10, and when the image forming apparatus 100 is operating, the upper face outlet 81b is directed towards the upper face of the case of the image forming apparatus 100.

On the other hand, in the ion generating apparatus 71D in Embodiment 4, as shown in FIGS. 12 and 13, a swiveling function is not provided in the ion generating apparatus 71D; instead, two outlets, namely an upper face outlet 81b and a front face outlet 81c, are provided, and switching of these outlets is performed mechanically.

That is, when the image forming apparatus 100 is in standby, switching is performed mechanically such that air including ions is blown out from the upper face outlet 81b, as shown in FIGS. 12 and 14, and when the image forming apparatus 100 is operating, switching is performed mechanically such that air including ions is blown out from the front face outlet 81c, as shown in FIGS. 13 and 15.

Specifically, in FIGS. 12 and 13, an outlet duct 84D that guides air delivered from the fan unit 82 to the upper face outlet 81b, or the front face outlet 81c, is formed between the fan unit 82 and the upper face outlet 81b and the front face outlet 81c.

As shown in FIGS. 12 and 13, the outlet duct 84D is provided with a movable duct front wall 95 and a movable duct rear wall 96. The movable duct front wall 95 extends from the front edge of the upper face outlet 81b to the front edge of the upper face of the fan unit 82, and has a plate-like shape that bulges slightly to the front face side. A movable duct front wall support shaft 95a is provided at the upper end of the movable duct front wall 95, and is rotatably supported at the front edge of the upper face outlet 81b. Arrow 97 in FIGS. 12 to 15 indicates the direction of rotation of the movable duct front wall.

The movable duct rear wall 96 extends from the center portion of the upper face of the fan unit 82 to the rear edge of the upper face outlet 81b, and has a plate-like shape that bulges slightly to the front face side. A movable duct front wall support shaft 96a is provided at the lower end of the movable duct front wall 96, and is rotatably supported in the center portion of the upper face of the fan unit 82. Arrow 98 in FIGS. 12 to 15 indicates the direction of rotation of the movable duct front wall.

As described above, the movable duct front wall 95 and the movable duct rear wall 96 are capable of pivoting, and in order to perform this pivoting, an unshown duct moving motor is provided within the outlet duct 84D. The duct moving motor is controlled by the control unit 74 of the image forming apparatus 100 shown in FIG. 1.

Other than the above, the ion generating apparatus 71D is the same as the ion generating apparatus 71C in Embodiment 3, as stated above. That is, in the lower portion within the ion generating apparatus 71D, ion generating elements 85 are provided on the front face side of the fan unit 82. These ion generating elements 85 and their arrangement are identical to those in the ion generating apparatus 71C in Embodiment 3.

Also, regarding control of the above ion generating apparatus 71D, other than control of the above duct moving motor, control of the fan 82a and the ion generating elements 85 is the same as in the ion generating apparatus 71C in Embodiment 3, and is performed by the control unit 74 of the image forming apparatus 100 shown in FIG. 1. As for the content of this control, as in the ion generating apparatus 71C in Embodiment 3, either the first control method or the second control method is performed, or both control methods are performed simultaneously in parallel.

In the above ion generating apparatus 71D in Embodiment 4, as in the ion generating apparatus 71C in Embodiment 3, as shown in FIGS. 12 and 13, due to the fan 82a mounted in the fan unit 82 rotating in the direction of arrow 87 indicating the direction of rotation, air drawn in via the intake holes 81a becomes air including positive and negative ions via the fan unit 82 and is emitted to the outside from the upper face outlet 81b or the front face outlet 81c, as described below.

In the above ion generating apparatus 71D, when the image forming apparatus 100 is in standby, as shown in FIG. 12, the lower end of the movable duct front wall 95 is stationary in a state positioned at the front edge of the upper face of the fan unit 82. The upper end of the movable duct rear wall 96 is stationary in a state positioned at the rear edge of the upper face outlet 81b.

Therefore, when the image forming apparatus 100 is in standby, as shown in FIG. 14, via the outlet duct 84D provided with the movable duct front wall 95 and the movable duct rear wall 96, which are stationary in the states described above, air including ions that has been delivered from the fan unit 82 rises along the movable duct front wall 95 and the movable duct rear wall 96, and is emitted to the outside from the upper face outlet 81b.

Air emitted from the upper face outlet 81b is emitted upward and scattered. Accordingly, air emitted from the upper face outlet 81b is scattered in the room where the image forming apparatus 100 is installed, and thus air in the room is purified.

On the other hand, when the image forming apparatus 100 is operating, as shown in FIG. 13, the lower end of the movable duct front wall 95 is stationary in a state positioned diagonally downward in front of the front face outlet 81c. The upper end of the movable duct rear wall 96 is stationary in a state positioned at the front edge of the upper face outlet 81b.

Therefore, when the image forming apparatus 100 is operating, as shown in FIG. 15, via the outlet duct 84D provided with the movable duct front wall 95 and the movable duct rear wall 96, which are stationary in the states described above, air including ions that has been delivered from the fan unit 82 rises along the movable duct rear wall 96 and also collides with the movable duct front wall 95, and along the movable duct front wall 95, is emitted to the outside from the front face outlet 81c.

Air emitted from the front face outlet 81c is emitted and scattered while directed diagonally downward in front of the front face outlet 81c. This direction diagonally downward to the front leads to the upper portion of the case of the image forming apparatus 100. Accordingly, air emitted from the front face outlet 81c is scattered around the case of the image forming apparatus 100, and thus harmful exhaust gas discharged from the case of the image forming apparatus 100 is purified.

The reason for adopting such a configuration is that like the ion generating apparatus 71C in Embodiment 3, the ion generating apparatus 71D in Embodiment 4 also is based on usage when the following sort of states are assumed.

That is, during operation of the image forming apparatus 100, the apparatus is mainly dedicated to purification of harmful exhaust gas discharged from the case of the image forming apparatus 100, and during standby of the image forming apparatus 100, the apparatus purifies air in the room where the image forming apparatus 100 has been installed.

According to the above ion generating apparatus 71D, same as the ion generating apparatus 71C in Embodiment 3, it is possible to provide the ion generating apparatus 71D external to the case of the image forming apparatus 100, so while suppressing increased size and cost of the image forming apparatus 100, it is possible to purify harmful exhaust gas discharged from the case of the image forming apparatus 100, and also possible to purify air in the room where the image forming apparatus 100 has been installed. That is, a single device can serve both the role of purifying exhaust gas from the case of the image forming apparatus 100, and purifying air within the room.

Also, by using the movable duct front wall 95 and the movable duct rear wall 96 provided in the ion generating apparatus 71D in Embodiment 4, it is possible to obtain the same operation and effects as the ion generating apparatus 71C in Embodiment 3.

Note that in the above ion generating apparatus 71D, the amount of ions generated and emitted by the ion generating apparatus 71D is less when the image forming apparatus 100 is operating than when the image forming apparatus 100 is in standby, but an operating method is also possible in which the amount of ions is the same when the image forming apparatus 100 is operating and when the image forming apparatus 100 is in standby.

Also, like the ion generating apparatus 71C, that is, like the ion generating apparatus 71A, which as shown in FIG. 6, can be attached to the case of the image forming apparatus 100 via the support column 72, which is provided protruding upward from the center portion on the upper side of the rear face of the case of the image forming apparatus 100, the ion generating apparatus 71D can be attached to the case of the image forming apparatus 100 via the support column 72A.

Other Embodiments

Above, embodiments of the invention have described with reference to the attached drawings, but the invention is of course not limited to the above embodiments.

For example, in the above embodiments, two states, when the image forming apparatus 100 is in standby and when the image forming apparatus 100 is operating, are described as operational states of the image forming apparatus 100. However, the operational states of the image forming apparatus 100 are not limited thereto; a configuration as described below may also be adopted.

That is, it is also possible to adopt a power-saving control in which, for example when a state in which the image forming apparatus 100 is not operated continues for a long time, the apparatus is switched from standby to a low-power state in which there is low power consumption, and furthermore switched from this low-power state to a sleep state in which there is even less power consumption, and again returned to the operating state when there is an instruction to perform image forming processing.

In such a case, it is possible to adopt a configuration in which air including ions is blown out from the upper face outlet 81b to purify air of the room in the above low-power state and sleep state as well, same as in the standby state.

A configuration may also be adopted in which the above ion generating apparatus 71 is attached later as optional equipment. In this case, a control unit for controlling the ion generating apparatus 71 is provided in the ion generating apparatus 71, and this control unit is connected to the control unit 74 of the image forming apparatus 100 by a serial communications cable.

By communications between the two control units, instructions are transmitted from the control unit 74 of the image forming apparatus 100 to the control unit of the ion generating apparatus 71, and control of the ion generating apparatus 71 is performed by the control unit of the ion generating apparatus 71.

Furthermore, the position where the ion generating apparatus 71 is attached may be changed according to the structure or usage circumstances of the image forming apparatus 100. For example, depending on the structure or usage circumstances of the image forming apparatus 100, a side face of the case of the image forming apparatus 100 may be disposed facing a wall or the like.

In this case, by adopting a configuration in which the support column 72 is provided protruding from a side wall of the case of the image forming apparatus 100, and the ion generating apparatus 71 is supported at the upper end of the support column 72, it is possible to prevent the ion generating apparatus 71 from hindering operation of the image forming apparatus 100.

Alternatively, a configuration may be adopted in which a support column 72 is not used; rather, the ion generating apparatus 71 is formed vertically, and directly attached to the case of the image forming apparatus 100. Also, a plurality of ion generating apparatuses 71 may be used, with these attached to the case of the image forming apparatus 100 in a dispersed manner.

The present invention may be embodied in various other forms without departing from the spirit or essential characteristics thereof. The embodiments disclosed in this application are to be considered in all respects as illustrative and not limiting. The scope of the invention is indicated by the appended claims rather than by the foregoing description, and all modifications or changes that come within the meaning and range of equivalency of the claims are intended to be embraced therein.

What is claimed is:

1. An image forming apparatus, comprising:
    a main body that performs processing to form an image on a recording paper;
    an ion generating section that is external to the main body, generates ions and emits those ions to the outside; and
    a control unit that controls the ion generating section in such a manner as to vary the amount of ions generated and emitted by the ion generating section, according to whether the main body is in an image forming state or in a non-image forming state,
    wherein the control unit controls the ion generating section such that the amount of ions generated and emitted by the ion generating section is less when the main body is in an image forming state than when the main body is in a non-image forming state,
    wherein the control unit further controls the ion generating section such that the ion generating section emits the generated ions at least towards the main body when the main body is in an image-forming state, and emits the generated ions at least in a direction other than towards the main body when the main body is in a non-image forming state.

2. The image forming apparatus according to claim 1, further comprising:
    an actuator that rotates the ion generating section such that the ion emission direction is switched between the direction towards the main body and the direction other than towards the main body.

3. The image forming apparatus according to claim 1, wherein
    a movable wall is provided within the ion generating section, and
    the image forming apparatus further comprises:
    an actuator that changes the position of the movable wall such that the ion emission direction is switched between the direction towards the main body and the direction other than towards the main body.

4. The image forming apparatus according to claim 1, wherein changing from the non-image forming state to the image forming state of the main body is performed due to generation of a signal from the control unit that instructs the main body to start the image forming processing, by a manual operation of the image forming apparatus or by transmission of the signal from an external apparatus connected to the control unit.

5. An image forming apparatus, comprising:
    a main body that performs processing to form an image on a recording paper;
    an ion generating section that is external to the main body, generates ions and emits those ions to the outside; and
    a control unit that controls the ion generating section such that the ion generating section emits the generated ions at least towards the main body when the main body is in an image forming state, and emits the generated ions at least in a direction other than towards the main body when the main body is in a non-image forming state.

* * * * *